United States Patent
Byun

(10) Patent No.: US 9,877,938 B2
(45) Date of Patent: Jan. 30, 2018

(54) MODIFIED TAURINE, AND PHARMACEUTICAL COMPOSITION FOR PREVENTING OR TREATING METABOLIC DISEASES CONTAINING SAME

(71) Applicant: Jonghyun Byun, Seoul (KR)

(72) Inventor: Jonghyun Byun, Seoul (KR)

( * ) Notice: Subject to any disclaimer, the term of this patent is extended or adjusted under 35 U.S.C. 154(b) by 0 days.

(21) Appl. No.: 15/414,322

(22) Filed: Jan. 24, 2017

(65) Prior Publication Data

US 2017/0165211 A1 Jun. 15, 2017

Related U.S. Application Data

(63) Continuation of application No. PCT/KR2015/013789, filed on Dec. 16, 2015.

(30) Foreign Application Priority Data

| Dec. 16, 2014 | (KR) | 10-2014-0181652 |
| Jan. 5, 2015 | (KR) | 10-2015-0000781 |
| Apr. 6, 2015 | (KR) | 10-2015-0048106 |
| Jul. 31, 2015 | (KR) | 10-2015-0108672 |

(51) Int. Cl.
| *A61K 31/18* | (2006.01) |
| *A61K 31/7004* | (2006.01) |
| *C07C 309/14* | (2006.01) |
| *A61K 9/00* | (2006.01) |
| *A61K 31/185* | (2006.01) |

(52) U.S. Cl.
CPC ........... *A61K 31/18* (2013.01); *A61K 9/00* (2013.01); *A61K 31/185* (2013.01); *A61K 31/7004* (2013.01); *C07C 309/14* (2013.01); *C07B 2200/13* (2013.01)

(58) Field of Classification Search
None
See application file for complete search history.

(56) References Cited

FOREIGN PATENT DOCUMENTS

| JP | 2000-119179 A | | 4/2000 |
| JP | 2000119179 | * | 4/2000 |
| JP | 2004-505056 A | | 2/2004 |
| JP | 2004505056 | * | 2/2004 |
| JP | 2005179215 | * | 7/2005 |
| JP | 2005-527234 A | | 9/2005 |
| JP | 2013-526488 A | | 6/2013 |
| KR | 10-2007-0023351 A | | 2/2007 |
| KR | 10-2010-0106289 A | | 10/2010 |

(Continued)

OTHER PUBLICATIONS

Cho et al., Bull. Korean Chem. Soc. 2014, vol. 35, No. 6 1863.*

(Continued)

*Primary Examiner* — Karl J Puttlitz
(74) *Attorney, Agent, or Firm* — Rothwell, Figg, Ernst & Manbeck, P.C.

(57) ABSTRACT

The present invention relates to a modified taurine, and a pharmaceutical composition for preventing or treating metabolic disease or a food composition, which contains the modified taurine as an active ingredient. More specifically, the modified taurine of the present invention has physical properties different from those of existing taurine, and has significant effects on the prevention and treatment of metabolic syndrome, including antithrombotic effects.

8 Claims, 29 Drawing Sheets

(56) References Cited

FOREIGN PATENT DOCUMENTS

KR    10-2011-0021690 A    3/2011
KR    10-2014-0022648 A    2/2014

OTHER PUBLICATIONS

Murakami, Amino Acids (2014) 46:73-80.*
Database CAPLUS Chemical Abstracts Service, Columbus, Ohio, US; Database Accession No. 2012:190245, Abstract of Lu et al., Hangzhou, Zhejiang, 310027, Peop. Rep. China.*
Machine Translation, retrieved from internet Apr. 18, 2017, retrieved from url: https://patents.google.com/patent/JP2004505056A/en.*
Yang, Jiao et al., "Determination and Correlation of the Solubility for Taurine in Water and Organic Solvent Systems," Journal of Chemical & Engineering Data, Apr. 23, 2010, vol. 55, pp. 2620-2623.
Cho, Hye Jeong et al., "Anti-Adipogenic Effect of Taurine-Carbohydrate Derivatives," Bulletin of the Korean Chemical Society, Jun. 2014, vol. 35, No. 6, pp. 1863-1866.
Search Report issued for International Application No. PCT/KR2015/013789 dated Apr. 12, 2016 (2 pages).

* cited by examiner

Melting point graph

Analysis report photograph

Start temperature: 200.0 °C
Stop temperature: 350.0 °C
Heating rate:     10.0°C /min
Onset point threshold: 70%
Single point threshold: 50%
Clear point threshold: 10%

|  | Left<br>Taurine | Right<br>ModifiedTaurine |
|---|---|---|
| Onset point | 328.9°C | 335.7°C |
| Single point | 334.4°C | 339.5°C |
| Clear point | 341.9°C | 344.8°C |

Test Results

| No. | Sample Name Provided by Client | Sample Name Used in Report | Sample Photograph |
|---|---|---|---|
| 1 | Taurine | Koptri-1551250-1 | |
| 2 | Modified Taurine | Koptri-1551250-2 | |

| Sample Name | Test Item | Test Method | Test Results | Remarks |
|---|---|---|---|---|
| Koptri-1551250-1 | Water Solubility | OECD Test Guideline 105 | 74 g/L (Freely Soluble) | By Flask Method |
| Koptri-1551250-2 | Water Solubility | OECD Test Guideline 105 | 77 g/L (Freely Soluble) | By Flask Method |

MODIFIED TAURINE, AND PHARMACEUTICAL COMPOSITION FOR PREVENTING OR TREATING METABOLIC DISEASES CONTAINING SAME

CROSS-REFERENCE TO RELATED APPLICATION

This application is a continuation application of International Application PCT/KR2015/013789 filed on Dec. 16, 2015 and designated the United States, which claims the benefit of Korean Patent Application No. 10-2014-0181652 filed on Dec. 16, 2014; Korean Patent Application No. 10-2015-0000781 filed on Jan. 5, 2015; Korean Patent Application No. 10-2015-0048106 filed on Apr. 6, 2015; and Korean Patent Application No. 10-2015-0108672 filed on Jul. 31, 2015, the disclosures of which are incorporated herein in their entirety by reference.

TECHNICAL FIELD

The present invention relates to a modified taurine and a pharmaceutical composition for preventing or treating metabolic disease, which contains the same as an active ingredient, and more particularly, to a pharmaceutical composition for preventing or treating metabolic disease, which contains a modified taurine having physical properties different from those of conventional taurine.

BACKGROUND ART

Obesity is a disease caused by excess body fat accumulation due to an imbalance between the body's energy intake and expenditure. Obesity leads to physical diseases, such as cardiovascular diseases, diabetes, hypertension, hyperlipidemia, gallstone disease, etc., and also affects mental health, and thus a countermeasure against obesity is urgently required (Kopelman P G. Obesity as medical problem. Nature 404: 635-643, 2000). Particularly, although the Orientals have a body mass index lower than that of Europeans, the Orientals have severe abdominal obesity, and thus are more susceptible to complications due to artery-related diseases such as hypertension, diabetes or hyperlipidemia, and for this reason, obesity management in the Orientals is more important.

Obesity which affects about 30-40% of modern persons is known as a strong risk factor that can cause hypertension, coronary artery disease, type II diabetes and various types of cancers. In obese persons, the risk of developing diseases is 4 times higher for hypertension and 10 times higher for diabetes than that in normal persons. Thus, obesity has a very close connection with the development of particularly diabetes.

In addition, thrombotic diseases together with obesity and diabetes are known as serious metabolic diseases. Thus, it is required to develop substances capable of more effectively preventing or treating metabolic diseases such as obesity, diabetes or thrombotic diseases.

Meanwhile, taurine, a type of food amino acid, is rarely found in plants, but is widely distributed in animals. It is known that taurine exhibits inhibitory activity against the sympathetic nerve of the brain to assist in blood pressure stabilization and stroke prevention, and inhibits the production of low-density lipoprotein (LDL) cholesterol that causes arteriosclerosis, angina, myocardial infarction or the like. In addition, taurine is known to be effective against adult diseases such as various vascular diseases and dementia, as well as intravascular platelet aggregation.

However, it is difficult to make taurine into useful modifications or compositions having therapeutic activity against various diseases, and thus taurine is currently generally used as a raw material for amino acid food without changes.

Accordingly, the present inventor has made extensive efforts, and as a result, has developed a pharmaceutical composition for preventing or treating metabolic disease, which contains a modified taurine.

DISCLOSURE

Technical Problem

The present invention has been made extensive efforts in order to solve the above-described problems occurring in the prior art, and it is an object of the present invention to provide a modified taurine and a preparation method thereof. Another object of the present invention is to provide a pharmaceutical composition for preventing or treating metabolic disease or a food composition, which contains the modified taurine as an active ingredient.

However, the technical object to be achieved by the present invention is not limited to the above technical object, and other objects that are not mentioned above can be clearly understood by those skilled in the art from the following description.

Technical Solution

Hereinafter, various embodiments described herein will be described with reference to figures. In the following description, numerous specific details are set forth, such as specific configurations, compositions, and processes, etc., in order to provide a thorough understanding of the present invention. However, certain embodiments may be practiced without one or more of these specific details, or in combination with other known methods and configurations. In other instances, known processes and preparation techniques have not been described in particular detail in order to not unnecessarily obscure the present invention. Reference throughout this specification to "one embodiment" or "an embodiment" means that a particular feature, configuration, composition, or characteristic described in connection with the embodiment is included in at least one embodiment of the present invention. Thus, the appearances of the phrase "in one embodiment" or "an embodiment" in various places throughout this specification are not necessarily referring to the same embodiment of the present invention. Additionally, the particular features, configurations, compositions, or characteristics may be combined in any suitable manner in one or more embodiments.

Unless otherwise specified in the specification, all the scientific and technical terms used in the specification have the same meanings as commonly understood by those skilled in the technical field to which the present invention pertains.

In one embodiment of the present invention, "taurine" refers to a type of food amino acid that is rarely found in plants but is widely distributed in animals. It is known that taurine exhibits inhibitory activity against the sympathetic nerve of the brain to assist in blood pressure stabilization and stroke prevention, and inhibits the production of low-density lipoprotein (LDL) cholesterol that causes arteriosclerosis, angina, myocardial infarction or the like. In addition, taurine is known to be effective against adult diseases such as various vascular diseases and dementia, as well as intravascular platelet aggregation. However, it is difficult to make taurine into useful modifications or compositions having therapeutic activity against various diseases, and thus taurine is currently used as a raw material for amino acid food without changes.

In one embodiment of the present invention, "modified taurine" refers to one that has physical properties different from those of conventional taurine due to its atypical structure. In addition, due to this difference in physical properties, the modified taurine has significant therapeutic effects against metabolic diseases.

The modified taurine differs from taurine with respect to physical property values, such as Raman spectrum, FT-IR spectrum, TGA, melting point or water solubility. Furthermore, the modified taurine is used as an active ingredient for a food or pharmaceutical formulation or used for synthesis of a pharmaceutical formulation, and it may be prepared by mixing taurine, water ($H_2O$) and a polar substance having a methyl group (—$CH_3$) in its molecular structure to produce a composition containing taurine, water ($H_2O$) and a polar substance having a methyl group (—$CH_3$) in its molecular structure and removing water and the polar substance from the composition.

In one embodiment of the present invention, "polarity" refers to the polarity of solvent, which is 9 for conventional substance, 5.2 for ethanol, 5.1 for methanol, 5.1 for acetone, 4 for propanol, and 4 for butanol. Depending on this difference in polarity between solvents, the solubility and physical properties of particles dissolved in the solvents may vary.

In one embodiment of the present invention, "obesity" refers to a condition having excess body fat, and a body fat corresponding to 25% or more of body weight for men or corresponding to 30% or more of body weight for women is defined as obesity. Obesity occurs when the calorie intake by food is more than the calorie consumption by activity, and thus lifestyle such as overeating and lack of exercise are the causes of obesity. This obesity is referred to as simple obesity. On the other hand, obesity may also be caused by a disease of the endocrine system, abnormalities in hypothalamus function, or abnormalities in energy metabolism, and this obesity is referred to as symptomatic obesity. In addition, the causes of obesity also include genetic factors. Obesity may be measured by height and bodyweight, and may also be diagnosed by measuring the thickness of skin wrinkles by use of calipers. Methods for calculating obesity index that indicates the degree of obesity include the modified Broca's method and body mass index (BMI). The modified Broca's method is a method of expressing current body weight as a percentage by calculating [height (cm)–100]×0.9 as ideal body weight. Namely, obesity in the modified Broca's method is equal to (actual body weight–ideal body weight)/ideal body weight×100%. The body mass index (BMI) is a value obtained by dividing body weight by square height. When current body weight is more than 20% of ideal body weight or BMI is 30 or more, it is referred to as obesity.

Obese people apparently look fat and may show breathlessness and joint pains. In addition, they may also show symptoms such as diabetes, hypertension or the like.

In one embodiment of the present invention, "diabetes" refers a disease caused by abnormalities in the relationship between glucose metabolism and blood glucose regulatory hormones in vivo. Diabetes is classified into insulin-dependent diabetes (type 1 diabetes), non-insulin-dependent diabetes (type 2 diabetes) and malnutrition-related-diabetes (MRDM). It has been reported that type 2 diabetes accounting for 90% or more of Korean diabetic patients is a metabolic disease characterized by high blood glucose levels and is caused either by the reduction in insulin secretion from pancreatic beta-cells by genetic, metabolic or environmental factors or by an increase in insulin resistance in peripheral tissue. In connection with this, it is known that the increase in body fat due to obesity leads to a decrease in insulin sensitivity, and particularly, abdominal fat accumulation is associated with glucose intolerance. Furthermore, it is known that obesity and insulin resistance in patients having type 2 diabetes have a close correlation with each other, and thus as obesity becomes more severe, insulin resistance also becomes more severe. Thus, insulin resistance improving agents capable of reducing insulin resistance, for example, thiazolidinedione-based drugs and biguanide, were developed as obesity therapeutic agents. Obesity therapeutic agents known to date include Xenical™ (Roche, Switzerland), Reductil™ (Abbott, USA), Exolise™ (Arkopharma, France), etc. However, because such agents show anti-obesity effects by appetite suppression and fat absorption rather than promoting fat burning and decomposition, these agents do not fundamentally solve insulin resistance problems, and cannot perfectly cure diabetes together with obesity, and have been reported to cause side effects, including heart diseases, respiratory diseases, nerve system diseases, etc.

In one embodiment of the present invention, "metabolic syndrome" refers to a disease in which various diseases, such as diabetes, hypertension, hyperlipidemia, obesity, coronary disease or arteriosclerosis, are caused by chronic metabolic disorder. It was first reported by Reaven (Reaven G M, Diabetes, 1988, 37:1595-1607) in 1988. Metabolic syndrome is characterized by insulin resistance, hypertension or dyslipidemia, and generally involves excess body weight or obesity. It was also reported that metabolic syndrome is the risk factor of cardiovascular disease and is associated with deaths by all causes. It was reported that the prevalence rate of metabolic syndrome in type 2 diabetic patients is higher than that in type 1 diabetic patients, and it is known that when type 2 diabetic patients have metabolic syndrome, the death rate thereof increases (Bonora E, et al. Diabet Med., 2004, 21:52-8; Ford E S, Diabetes Care., 2005, 28:1769-78; Alexander C M, et al. Diabetes, 2003, 52:1210-1214). In addition, studies on the correlation of macrovascular and microvascular complications of type 2 diabetes with the components of metabolic syndrome, such as hypertension, dyslipidemia or the like, were reported (Mykkanen L, et al. Diabetologia., 1993, 36:553-559; Haffner S M, et al. Diabetes, 1992, 41:715-722). The most serious problem of metabolic syndrome is the development of chronic complications, such as diabetic retinopathy, nephropathy, neuropathy, hyperlipidemia, or cardiovascular diseases (stroke, angina, myocardial infarction, peripheral vascular diseases) (Wolf S P, Br Med Bull., 1993, 49:642-652). Such chronic complications mostly undergo an irreversible progressive process after their development, and a method capable of completely blocking this process is not yet present. Thus, when suitable treatment of metabolic syndrome is not performed, serious symptoms are caused, leading to death of the patient. Thus, for effective control or treatment of metabolic syndrome having a combination of symptoms, it is ideal to have the effect of treating nephropathy, hepatic disease, hyperlipidemia or the like together with a blood glucose lowering effect for maintaining normal blood glucose levels. However, a therapeutic agent having such effects has not yet been developed, and blood glucose lowering agents, blood pressure lowering agents, cholesterol lowering agents and the like have been separately administered.

Korean Unexamined Patent Application Publication No. 2008-0059575 discloses a salt of a PPAR regulator and a method for treating metabolic disease. However, the salt may cause side effects, because it is a chemical synthetic product. In an attempt to minimize such side effects, Korean Unexamined Patent Application Publication No. 2009-0114093 discloses a composition for preventing or treating obesity and metabolic syndrome or syndrome X, which contains, as an active ingredient, a mixed extract of *Evodiae fructus, Imperatae rhizome* and *Citrus Unshiu* Markovich, and Korean Unexamined Patent Application Publication No. 2010-0956278 discloses a composition for treating or preventing diabetes and diabetic complications, which contains, as an active ingredient, a mixed extract of herbal plants, including *Momordica charantia, Cordyceps sinensis, Lycii Radicis* cortex, *Morus alba, Euonymus alatus, Pueraria lobata, Polygonatum sibiricum, Atractylodes macrocephala, Liriope platyphylla, Corni fructus*, and *ginseng*.

In one embodiment of the present invention, "blood coagulation" means that blood coagulates after leakage from blood vessels. Blood in the human body functions to carry oxygen, nutrients, and wastes, and has various important functions, including buffering, body temperature maintenance, osmotic pressure control, ion balance maintenance, constant water content maintenance, humoral control, blood pressure maintenance and control, and host defense.

As reported in the art, in normal blood circulation, the blood coagulation system and the thrombolytic system in vivo are controlled complementarily to each other to facilitate blood circulation. In the mechanism of the blood coagulation system among these systems, platelets adhere to blood vessel walls and aggregate to form platelet thrombi, and then the blood coagulation system is activated, and fibrin thrombi are formed with respect to platelet aggregate masses. In production of fibrin thrombi, thrombin that is involved in fibrin coagulation are activated by multi-step reactions of many blood coagulation factors to produce fibrin monomers from fibrinogen, and the fibrin monomers are polymerized by calcium to form fibrin polymers that bind to platelets and endothelial cells and that are cross-linked by XIII factor, thereby producing permanent thrombi. Thus, a substance that inhibits thrombin activity may be used as a very useful preventive and therapeutic agent against various thrombotic diseases that are caused by excessive blood coagulation abnormalities. It is known that prothrombin activation following the sequential activation of XII factor, XI factor, IX factor and X factor in the endogenous thrombus formation pathway finally activates thrombin. Thus, specific inhibition of blood coagulation factors also becomes an important target for the development of agents for treating thrombotic diseases. Until now, various anticoagulants, anti-platelet agents or thrombolytic agents, including heparin, coumarin, aspirin, urokinase and the like, have been used for the prevention and treatment of thrombotic diseases. However, these agents are very expensive, and the use thereof is limited due to hemorrhagic side effects, gastrointestinal disorder and hypersensitivity.

In one embodiment of the present invention, "pharmaceutical composition" refers to a composition to be administered for a specific purpose. For the purpose of the present invention, the pharmaceutical composition of the present invention contains the modified taurine, and is administered for the prevention or treatment of metabolic disease, and may contain sugar, protein and a pharmaceutically acceptable carrier, excipient or diluent, which are involved therein. The "pharmaceutically acceptable" carrier or excipient means approved by a regulatory agency of the Federal or a state government, or as listed in the pharmacopoeia or other generally recognized pharmacopoeia for use in vertebral animals, and more particularly in humans.

The pharmaceutical compositions containing the modified taurine, suitable for parenteral administration, can be in the form of suspensions, solutions, or emulsions, in oily or aqueous vehicles, and can contain formulatory agents such as suspending, stabilizing, solubilizing, and/or dispersing agents. This form can be sterile and can be fluid. It can be stable under the conditions of manufacture and storage and can be preserved against the contaminating action of microorganisms such as bacteria and fungi. Alternatively, the pharmaceutical composition containing the modified taurine can be in sterile powder form for reconstitution with a suitable vehicle before use. The pharmaceutical composition can be presented in unit dose form, in ampoules, or other unit-dose containers, or in multi-dose containers. Alternatively, the pharmaceutical composition can be stored in a freeze-dried (lyophilized) condition requiring only the addition of sterile liquid carrier, for example, water for injection immediately prior to use. Extemporaneous injection solutions and suspensions can be prepared from sterile powders, granules or tablets.

Excipients that are suitable for the pharmaceutical composition containing the modified taurine include preservatives, suspending agents, stabilizers, dyes, buffers, antibacterial agents, antifungal agents, and isotonic agents, for example, sugars or sodium chloride. As used herein, the term "stabilizer" refers to a compound optionally used in the pharmaceutical composition of the present invention in order to avoid the need for sulfite salts and increase storage life. Non-limiting examples of stabilizers include antioxidants.

The pharmaceutical composition can comprise one or more pharmaceutically acceptable carriers. The carrier can be a solvent or dispersion medium. Non-limiting examples of pharmaceutically acceptable carriers include water, saline, ethanol, polyol (e.g., glycerol, propylene glycol and liquid polyethylene glycol), oils, and suitable mixtures thereof.

The parenteral formulation can be sterilized. Non-limiting examples of sterilization techniques include filtration through a bacterial-retaining filter, terminal sterilization, incorporation of sterilizing agents, irradiation, heating, vacuum drying, and freeze drying.

Furthermore, the pharmaceutical composition according to the present invention can be prepared by adding one or more, selected from the group consisting of sugar, polyphenol and amino acid, to the modified taurine or "a composition containing taurine, water and a polar substance having a methyl group ($-CH_3$) in its molecular structure" that produces the modified taurine. Herein, the sugar may be selected from the group consisting of monosaccharides, disaccharides and polysaccharides. In this case, the molar ratios between taurine and sugar and between taurine and polyphenol and between taurine and amino acid in the modified taurine or "the composition containing taurine, water and a polar substance having a methyl group ($-CH_3$) in its molecular structure" that produces the modified taurine are preferably 0.1-3.5:0.01-3.5, 0.1-3.5:0.001-3.5, and 0.1-3.5:0.01-3.5, respectively, but are not limited thereto.

In one embodiment of the present invention, "food composition" refers to a food composition that is used to alleviate metabolic disease in various ways. The food composition containing the composition of the present invention as an active ingredient can be prepared as various foods, for example, beverages, gums, teas, vitamin complexes, powders, granules, tablets, capsules, confectionery, cakes, bread and the like. The food composition of the present invention is an improved food composition obtained based on a conventional food composition having little or no toxicity and side effects, and thus can be used without anxiety for preventive purposes over a long period of time. When the composition of the present invention is included in a food composition, it may be added in an amount of 0.1-100 wt % based on the total weight. When the food composition is prepared as a beverage, there is no particular limitation, except that the beverage contains the food composition at the indicated percentage. The beverage may additionally contain various flavorings or natural carbohydrates as in conventional beverages. Examples of the natural carbohydrates include monosaccharides such as glucose, disaccharides such as fructose, polysaccharides such as sucrose, conventional sugars such as dextrin, cyclodextrin or the like, and sugar alcohols such as xylitol, sorbitol, erythritol or the like. Examples of the flavorings include natural flavorings (thaumatin, stevia extracts, such as rebaudioside A, glycyrrhizin, etc.) and synthetic flavorings (saccharin, aspartame, etc.).

In addition, the food composition of the present invention may contain various nutrients, vitamins, minerals (electrolytes), flavorings such as synthetic flavorings and natural flavorings, colorants, pectic acid and its salt, alginic acid and its salt, organic acids, protective colloidal thickeners, pH adjusting agents, stabilizers, preservatives, glycerin, alcohol, carbonizing agents as used in carbonated beverages, etc. Such components may be used individually or in combination. Although the percentage of such additives is not of great importance, it is generally selected in a range of 0.1 to about 100 parts by weight based on 100 parts by weight of the composition of the present invention.

In one embodiment of the present invention, "administration" means introducing the composition of the present invention into a patient by any suitable method. The composition of the present invention may be administered by any general route, as long as it can reach a target tissue. Specifically, the composition of the present invention may be administered orally, intraperitoneally, intravenously, intramuscularly, subcutaneously, intradermally, intranasally, intrapulmonarily, intrarectally, intracavitally or intrathecally. However, a pharmaceutical composition for preventing or treating metabolic disease, which contains the modified taurine according to the present invention, is preferably administered orally or intravenously, but is not limited thereto.

A method for treating metabolic disease according to the present invention may comprise administering a pharmaceutically effective amount of the pharmaceutical composition. In the present invention, the effective amount can be determined depending on various factors, including the kind of disease, the severity of the disease, the kinds and contents of active ingredient and other ingredients in the composition, the kind of formulation, the patient's age, body weight, general health condition, sex and diet, the time of administration, the route of administration, the secretion rate of the composition, the period of treatment, and other drugs that are concurrently used.

In one embodiment of the present invention, there is provided a modified taurine produced by dissolving taurine with heating in a first polar solvent and adding a second polar solvent thereto, wherein the difference in polarity between the first solvent and the second solvent is 5 or less, and wherein the strength ratios of absorption bands of 891/847, 1182/1256 and 1427/1458 at 847, 891, 1182, 1256, 1427 and 1458 $cm^{-1}$ in the Raman spectrum of the modified taurine are all less than 1. In the embodiment, an onset point where the modified taurine starts to melt ranges from 330° C. to 340° C., and the water solubility of the modified taurine is 75-79 g/L. Furthermore, the absorption wavelength at 1650-2800 $cm^{-1}$ in the FT-IR spectrum of the modified taurine differs from that of the taurine. In addition, the first polar solvent is water, and the second polar solvent contains a methyl group ($—CH_3$). Furthermore, the second polar solvent may be any one or more selected from the group consisting of methanol, ethanol, butanol, acetic acid, acetone, propanol, chloroform, and ethyl acetate.

In one embodiment, there is provided a pharmaceutical composition for preventing or treating metabolic disease, which contains the modified taurine as an active ingredient. In the embodiment, the metabolic disease is diabetes, obesity or thrombotic disease. The thrombotic disease is one or more selected from the group consisting of myocardial infarction, ischemic stroke, hemorrhagic stroke, pulmonary thrombosis, deep vein thrombosis, peripheral vascular occlusion, portal vein thrombosis, renal vein occlusion, cerebral venous sinus thrombosis, peripheral neuropathy, peripheral vascular disease, nephropathy, and central retinal vascular occlusion. The pharmaceutical composition may further contain any one or more selected from the group consisting of sugar, polyphenol and amino acid. The sugar may be any one or more selected from the group consisting of ketotriose, aldotriose, ketotetrose, aldotetrose, ribulose, xylose, ribose, arabinose, mannose, fructose, glucose, sucrose, lactose, maltose, trehalose, inulin, and cellulose. The polyphenol may be any one or more selected from the group consisting of flavanol, flavone, isoflavone, flavonol, flavanone, anthocyanin, aurone, chalcone, dihydrochalcone, and derivatives thereof. The amino acid may be any one or more selected from the group consisting of betaine, glycine, ornithine, proline, dimethylglycine, aspartic acid, glutamic acid, leucine, and methionine. The molar ratio between the taurine and the sugar is 0.1-3.5:0.01-3.5, the molar ratio between the taurine and the polyphenol is 0.1-3.5:0.001-3.5, and the molar ratio between the taurine and the amino acid is 0.1-3.5:0.01-3.5.

In one embodiment of the present invention, there is provided a method for producing a modified taurine, comprising the steps of: dissolving taurine with heating in a first polar solvent; and adding a second polar solvent thereto to produce the modified taurine, wherein the difference in polarity between the first solvent and the second solvent is 5 or less, the first polar solvent is water, and the second polar solvent contains a methyl group ($—CH_3$). In the embodiment, the second polar solvent may be any one or more selected from the group consisting of methanol, ethanol, butanol, acetic acid, acetone, propanol, chloroform, and ethyl acetate. In the method, the strength ratios of absorption bands of 891/847, 1182/1256 and 1427/1458 at 847, 891, 1182, 1256, 1427 and 1458 $cm^{-1}$ in the Raman spectrum of the modified taurine are all less than 1. In the embodiment, an onset point where the modified taurine starts to melt ranges from 330° C. to 340° C., and the water solubility of the modified taurine is 75-79 g/L. Furthermore, the absorption wavelength at 1650-2800 $cm^{-1}$ in the FT-IR spectrum of the modified taurine differs from that of the taurine.

In one embodiment of the present invention, there is provided a food composition for improving or alleviating metabolic disease, which contains the modified taurine.

In one embodiment of the present invention, heating or warming may be direct heating or may be performed using any method capable of heating water, for example, a microwave oven. Removal of the "polar substance having a methyl group (—$CH_3$) in its molecular structure" may also be performed using any method such as a heating method, a separation method or the like. When the heating method is used and the polar substance is alcohol, the alcohol is removed by heating it above the boiling point thereof (about 78.4° C. for ethanol, and about 64.7° C. for methanol). Where the polar substance is ethanol, it is removed by heating at about 100° C. for about 1-15 minutes when the volume of the ethanol-containing mixture is 100 ml.

In one example of the present invention, taurine ($NH_2CH_2CH_2SO_3H$) was dissolved in purified water, and then "a polar substance having a methyl group (—$CH_3$) in its molecular structure" was added thereto, in order to confirm that is it possible to produce "a composition containing taurine, water and a polar substance having a methyl group (—$CH_3$) in its molecular structure" required for production of a modified taurine that has physical properties different those of conventional taurine, and thus may be used as an active ingredient in a pharmaceutical formulation or may be used for synthesis of a pharmaceutical formulation.

In one example of the present invention, water was heated to increase the solubility of taurine to thereby make an aqueous taurine solution at the boiling point, and alcohol or acetone, which is a polar substance having a methyl group (—$CH_3$) in its molecular structure, was added to the aqueous taurine solution, thereby preparing "a composition containing taurine, water and a polar substance having a methyl group (—$CH_3$) in its molecular structure" comprising a formed white semi-solid material that produces "a modified taurine" (see FIG. 1). The white semi-solid material consists of taurine, water and alcohol (or acetone), and when alcohol (or acetone) is removed therefrom, a modified taurine is produced. Namely, when water and "the polar substance having a methyl group (—$CH_3$) in its molecular structure" are removed from "the composition containing taurine, water and a polar substance having a methyl group (—$CH_3$) in its molecular structure" comprising a formed white semi-solid material, a modified taurine having physical properties different from those of conventional taurine is produced.

In one embodiment of the present invention, "the polar substance or solvent having or containing a methyl group (—$CH_3$)" includes "a polar substance containing an alkyl group (CnH2n+1) such as a methyl group (—$CH_3$)" such as alcohol, and should have suitable polarity so that it can form the white semi-solid material that produces "the modified taurine", when it is mixed with an aqueous taurine solution. The white semi-solid material is a material formed of taurine, water and "the polar substance having a methyl group (—$CH_3$) in its molecular structure". Examples of "a polar substance having a methyl group (—$CH_3$) in its molecular structure" that may be used in the present invention methanol, ethanol, butanol, acetone and the like. However, as the carbon number of alcohol increases, the polarity thereof decreases rapidly, and thus the amount of white semi-solid material formed decreases. Thus, this fact should be taken into consideration. "The composition containing taurine, water and a polar substance having a methyl group (—$CH_3$) in its molecular structure" that produces "the modified taurine" can generally be prepared by adding 0.1-17.1 g of taurine to 30 ml of purified water at 1 atm, dissolving the taurine by heating to 100° C., and adding and mixing 1-1000 ml of "a polar substance having a methyl group (—$CH_3$) in its molecular structure" to the taurine solution. If the amount of taurine added is smaller than the lower limit of the above-described range, its function as an intermediate for synthesis of a pharmaceutical formulation, that is, the desired therapeutic effect of the final pharmaceutical composition, can be reduced, and if the amount of taurine added is larger than the upper limit of the above-described range, a problem will arise in that the taurine is not properly dissolved. In addition, the amount of "the polar substance having a methyl group (—$CH_3$) in its molecular structure" added is smaller than the lower limit of the above-described range, the modified taurine will not be sufficiently formed. The amount of "the polar substance having a methyl group (—$CH_3$) in its molecular structure" added is not particularly limited, as long as the modified taurine can be sufficiently produced; however, the polar substance having a methyl group (—$CH_3$) in its molecular structure is preferably added in an amount of 10-3000 parts by weight based on 100 parts by weight of the aqueous taurine solution.

Advantageous Effects

The modified taurine according to the present invention and a pharmaceutical composition for preventing or treating metabolic disease, which contains the same as an active ingredient, are effective in reducing triglyceride levels and have anti-thrombotic effects. Thus, the modified taurine and the composition will greatly contribute to the prevention and treatment of metabolic syndrome.

DESCRIPTION OF DRAWINGS

FIG. 7 shows the results of measuring the water solubilities of taurine and a modified taurine according to an example of the present invention.

FIGS. 20 to 23 shows photographs of the liver, white adipose tissue (WAT), brown adipose tissue (BAT) and kidney tissue of mice treated with the pharmaceutical composition of the present invention according to an example of the present invention.

BEST MODE

Figure 1:
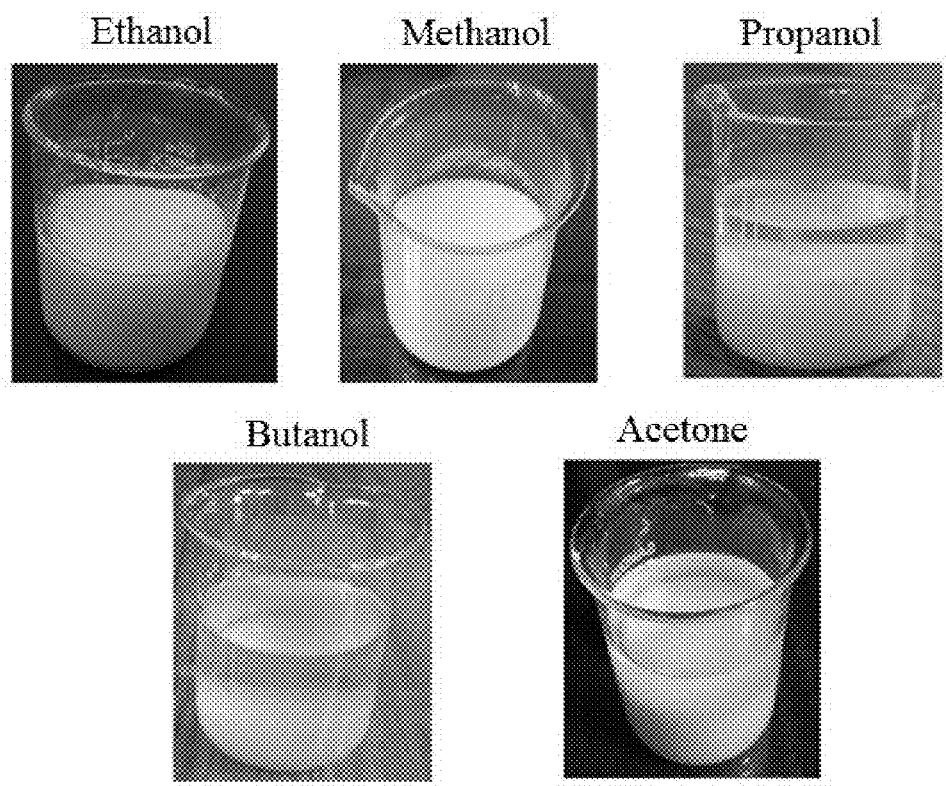
FIG. 1 shows photographs of "a composition containing taurine, water and a polar substance having a methyl group (—$CH_3$) in its molecular structure, which is prepared by mixing taurine, water and a polar substance having a methyl group (—$CH_3$) in its molecular structure according to an example of the present invention and comprises a formed white semi-solid material that produces a modified taurine".

In one embodiment of the present invention, there is provided a modified taurine produced by dissolving taurine with heating in a first polar solvent and adding a second polar solvent, wherein the difference in polarity between the first solvent and the second solvent is 5 or less, and wherein the strength ratios of absorption bands of 891/847, 1182/1256 and 1427/1458 at 847, 891, 1182, 1256, 1427 and 1458 cm$^{-1}$ in the Raman spectrum of the modified taurine are all less than 1.

In another embodiment of the present invention, there is provided a pharmaceutical composition for preventing or treating metabolic disease, which contains the modified taurine as an active ingredient.

In still another embodiment of the present invention, there is provided a method for producing a modified taurine, comprising the steps of: dissolving taurine with heating in a first polar solvent; and adding a second polar solvent thereto to produce the modified taurine, wherein the difference in polarity between the first solvent and the second solvent is 5 or less, the first polar solvent is water, and the second polar solvent contains a methyl group (—CH$_3$).

In yet another embodiment of the present invention, there is provided a food composition for improving or alleviating metabolic disease, which contains the modified taurine.

MODE FOR INVENTION

Hereinafter, the present invention will be described in further detail. It will be obvious to those skilled in the art that these examples are for illustrative purposes only and are not intended to limit the scope of the present invention.

Design of Compositions

Prior to experiments, the components and component ratios of examples and comparative examples to be used in each experiment were designed. The results of the design are shown in Table 1 below. Specific methods for preparation of each component and composition are described in Examples 1 and 2 and Comparative Examples 1 and 2.

TABLE 1

| Example 1-2 | TauAlc | DT15 |
|---|---|---|
| Example 2-1 | TauAlc 8.6* + Ara 2.5 | DT16 |
| | TauAlc 8.6 + Xyl 3.5 | DT20 |
| Example 2-2-1 | TauAlc 8.6 + Ara 1.04 | |
| | TauAlc 8.6 + Ara 5.2 | |
| | TauAlc 8.6 + Ara 7.8 | |
| | TauAlc 8.6 + Xyl 1.04 | |
| | TauAlc 8.6 + Xyl 5.2 | |
| | TauAlc 8.6 + Xyl 7.8 | |
| | TauAlc 4.3 + Rib 2.6 | |
| | TauAlc 4.3 + Rib 6.5 | |
| Example 2-2-2 | TauAlc 8.6 + Ara 1.04 | |
| | TauAlc 8.6 + Ara 5.2 | |
| | TauAlc 8.6 + Ara 7.8 | |
| | TauAlc 8.6 + Xyl 1.04 | |
| | TauAlc 8.6 + Xyl 5.2 | |
| | TauAlc 8.6 + Xyl 7.8 | |

TABLE 1-continued

| Example 2-3 | TauAlc 4.3 + Glu 3.1 | |
|---|---|---|
| | TauAlc 4.3 + Glu 7.75 | |
| | TauAlc 4.3 + Mann 3.1 | |
| | TauAlc 4.3 + Mann 7.75 | |
| | TauAlc 4.3 + Fruc 7.75 | |
| Example 2-4-1 | TauAlc 8.6 + Cat 3 + Bet 4 | DT7 |
| Example 2-4-2 | TauAlc 8.6 + EGCG 1.5 + Bet 4 | DT10 |
| Example 2-5 | TauAlc 8.6 + EGCG 1.5 + Bet 4 + Xyl 3.5 | DT4 |
| Comparative Example 1 | Tau** | DT19 |
| Comparative Example 2-1 | Ara 1.04 | |
| | Ara 5.2 | |
| | Ara 7.8 | |
| | Xyl 1.04 | |
| | Xyl 5.2 | |
| | Xyl 7.8 | |
| | Rib 5.2 | |
| | Rib 10.4 | |
| Comparative Example 2-2 | Glu 6.2 | |
| | Glu 12.4 | |
| | Mann 3.1 | |
| | Mann 6.2 | |
| | Mann 12.4 | |
| | Fruc 6.2 | |
| | Fruc 12.4 | |
| Comparative Example 2-3-1 | Tau 8.6 + Ara 1.04 | |
| | Tau 8.6 + Ara 5.2 | |
| | Tau 8.6 + Ara 7.8 | |
| | Tau 8.6 + Xyl 1.04 | |
| | Tau 8.6 + Xyl 5.2 | |
| | Tau 8.6 + Xyl 7.8 | |
| | Tau 4.3 + Rib 2.6 | |
| | Tau 4.3 + Rib 6.5 | |
| Comparative Example 2-3-2 | Tau 8.6 + Ara 2.5 | DT18 |
| | Tau 8.6 + Xyl 3.5 | DT21 |
| Comparative Example 2-4 | Tau 4.3 + Glu 3.1 | |
| | Tau 4.3 + Glu 7.75 | |
| | Tau 4.3 + Mann 3.1 | |
| | Tau 4.3 + Mann 7.75 | |
| | Tau 4.3 + Fruc 7.75 | |
| Comparative Example 2-5-1 | Tau 8.6 + Cat 3 + Bet 4 | DT11 |
| Comparative Example 2-5-2 | Tau 8.6 + EGCG 1.5 + Bet 4 | DT14 |
| Comparative Example 2-6 | Tau 8.6 + EGCG 1.5 + Bet 4 + Xyl 3.5 | DT6 |

*TauAlc 8.6 means 8.6 g of modified taurine.
**Tau is conventional taurine.

In the above table, Tau: taurine, TauAlc: modified taurine, Ara: arabinose, Xyl: xylose, Rib: ribose, Glu: glucose, Mann: mannose, Fruc: fructose, Cat: catechin, Bet: betaine, EGCG: epigallocatechin gallate.

Example 1: Preparation of Modified Taurine 1-1: Preparation of Composition Containing Modified Taurine Taurine (8.6 g) was added to 30 ml of purified water and dissolved by heating in a microwave oven for about 60 seconds, and then immediately, the solution was stirred with a rod while 60 ml of alcohol (ethanol (ethanol was used hereinafter), methanol, propanol or butanol) or acetone was added thereto, thereby preparing compositions (FIG. 1) which are mixtures comprising a white semi-solid material.

1-2: Preparation of Modified Taurine Crystal (1) Taurine (1.72 g) was added to 6 ml of purified water, or (2) taurine (4.3 g) was added to 15 ml of purified water, or (3) taurine (8.6 g) was added to 28 ml of purified water. The added taurine was dissolved by heating in a microwave oven for 20-60 seconds, and then immediately, the taurine solution was stirred with a rod while 12 ml of ethanol (for (1) above), 30 ml of ethanol (for (2) above) or 60 ml of ethanol (for (3) above) was added at room temperature, thereby preparing mixtures comprising a formed semi-solid material.

Next, 40 ml of purified water or 32 ml of purified water (for (3) above), heated to about 100° C., was added to each of the prepared mixtures, and then heated in a microwave oven for about 3-5 minutes until the alcohol was removed, thereby preparing compositions.

A solid taurine crystal was prepared according to the case of (3) above, and then dried in a hot-air dryer. (See Table 1 above for the specific component ratio of each composition).

Example 2: Preparation of Pharmaceutical Compositions for Prevention or Treatment of Metabolic Disease 2-1: Preparation 1 of Modified Taurine+Pentose Composition A predetermined amount (2.5 g or 3.5 g) of pentose (xylose or arabinose) was added to 32 ml of purified water and completely dissolved by heating in a microwave oven for 30 seconds. Meanwhile, taurine (8.6 g) was added to 28 ml of purified water and dissolved by heating in a microwave oven for 60 seconds, and then immediately, the taurine solution was stirred with a rod while 60 ml of ethanol was added, thereby preparing a mixture comprising a formed white semi-solid material. Next, each of the aqueous pentose solutions prepared as described above was added to the mixture, and then heated in a microwave oven for about 5 minutes until the alcohol was completely removed, thereby preparing compositions. (See Table 1 above for the specific component ratio of each composition).

2-2-1: Preparation 2 of Modified Taurine+Pentose Composition

A predetermined amount (1.04 g, 2.6 g, 5.2 g, 6.5 g or 7.8 g) of pentose (xylose, arabinose or ribose) was added to 40 ml of purified water and completely dissolved by heating in a microwave oven for about 30-50 seconds. Meanwhile, (1) taurine (4.3 g) was added to 15 ml of purified water, or (2) taurine (8.6 g) was added to 30 ml of purified water, and the added taurine was dissolved by heating in a microwave oven for 40-60 seconds, and then immediately, the taurine solution was stirred with a rod while 30 ml (for (1) above) or 60 ml (for (2) above) of ethanol was added thereto, thereby preparing mixtures comprising a formed white semi-solid material. Next, the aqueous pentose solution prepared as described above was added to the mixture, and then heated in a microwave oven for about 3-5 minutes until the alcohol was completely removed. Purified water was added to the mixture to a total volume of 100 ml before use in experiments. (See Table 1 above for the specific component ratio of each composition).

2-2-2: Preparation 3 of Modified Taurine+Pentose Composition 40 ml of purified water was boiled by heating in a microwave oven for about 30 seconds. Then, taurine (8.6 g) was added to 30 ml of purified water and dissolved by heating in a microwave oven for about 60 seconds, and then immediately, the taurine solution was stirred with a rod while 60 ml of ethanol was added thereto, thereby preparing a mixture comprising a formed white semi-solid material. Next, 40 ml of the boiled purified water prepared as described above was added to the mixture, and then heated in a microwave oven at 100° C. for about 5 minutes until the alcohol was completely removed, thereby preparing a composition.

Furthermore, a predetermined amount (1.04 g, 5.2 g or 7.8 g) of pentose (xylose or arabinose) was added to 40 ml of purified water and completely dissolved by heating in a microwave oven for about 30 seconds. To the solution, the composition prepared as described above was added, and the mixture was heated in a microwave oven for about 30 seconds, after which purified water was added to the mixture to a total volume of 100 ml before use in experiments. (See Table 1 above for the specific component ratio of each composition).

2-3: Preparation of Modified Taurine+Hexose Composition

A predetermined amount (3.1 g or 7.75 g) of hexose (mannose, glucose or fructose) was added to 40 ml of purified water and completely dissolved by heating in a microwave oven for about 50 seconds. Meanwhile, taurine (4.3 g) was added to 15 ml of purified water and dissolved by heating in a microwave oven for about 40 seconds, and then immediately, the taurine solution was stirred with a rod while 30 ml of ethanol was added thereto, thereby preparing a mixture comprising a formed white semi-solid material. Next, the aqueous hexose solution prepared as described above was added to the mixture, and then heated in a microwave oven for about 3 minutes and 30 seconds until the alcohol was completely removed, after which purified water was added to the mixture to a total volume of 100 ml before use in experiments. (See Table 1 above for the specific component ratio of each composition).

2-4-1: Preparation 1 of Modified Taurine+Polyphenol+Amino Acid Composition

Taurine (8.6 g) was added to 30 ml of purified water and completely dissolved by heating in a microwave oven for about 1 minute and 20 second, and then immediately, the taurine solution was stirred with a rod while 60 ml of ethanol was added thereto, thereby preparing a mixture comprising a formed white semi-solid material. Next, 40 ml of purified water was heated to about 100° C. in a microwave oven for 1 minute, and catechin (3 g) and betaine (4 g) were added thereto and dissolved, after which the solution was added to the mixture, and then heated in a microwave oven for 5 minutes to remove the ethanol. (See Table 1 above for the specific component ratio of each composition).

2-4-2: Preparation 2 of Modified Taurine+Polyphenol+Amino Acid Composition

Taurine (8.6 g) was added to 30 ml of purified water and completely dissolved by heating in a microwave oven for about 1 minute and 20 second, and then immediately, the taurine solution was stirred with a rod while 60 ml of ethanol was added thereto, thereby preparing a mixture comprising a formed white semi-solid material. Meanwhile, 40 ml of purified water was heated to about 100° C. in a microwave oven for 1 minute, and EGCG (1.5 g) and betaine (4 g) were added thereto and dissolved, after which the solution was added to the mixture, and then heated in a microwave oven for 5 minutes to remove the ethanol. (See Table 1 above for the specific component ratio of each composition).

2-5: Preparation of Modified Taurine+Polyphenol+Amino Acid Composition+Pentose Composition Taurine (8.6 g) was added to 30 ml of purified water and completely dissolved by heating in a microwave oven for about 1 minute and 20 second, and then immediately, the taurine solution was stirred with a rod while 60 ml of ethanol was added thereto, thereby preparing a mixture comprising a formed white semi-solid material. Meanwhile, 40 ml of purified water was heated to about 100° C. in a microwave oven for 1 minute, and EGCG (1.5 g), betaine (4 g) and xylose (3.5 g) were added thereto and dissolved, after which the solution was added to the mixture, and then heated in a microwave oven for 5 minutes to remove the ethanol. (See Table 1 above for the specific component ratio of each composition).

Comparative Example 1: Preparation of Aqueous Taurine Solution 1-1: Preparation 1 of Aqueous Taurine Solution 60 ml of taurine was heated in a microwave oven for about 1 minute, and taurine (8.6 g) was added and dissolved, and then heated in a microwave oven for 3 minutes.

1-2: Preparation 2 of Aqueous Taurine Solution 40 ml of purified water was boiled by heating in a microwave oven for about 30 seconds. Meanwhile, taurine (1.72 g, 4.3 g or 8.6 g) was added to 30 ml of purified water and dissolved by heating to 100° C. in a microwave oven for 1 minute. The taurine solution was added to 40 ml of the boiled purified water prepared as described above, and was heated to boiling in a microwave oven for about 2 minutes, after which purified water was added to the mixture to a total volume of 100 ml before use in experiments. (See Table 1 above for the specific component ratio of each composition).

Comparative Example 2: Preparation of Pharmaceutical Compositions for Prevention or Treatment of Metabolic Disease 2-1: Preparation of Pentose Composition A predetermined amount (1.04 g, 5.2 g, 7.8 g or 10.4 g) of pentose (xylose, arabinose or ribose) was added to 40 ml of purified water and completely dissolved by heating in a microwave oven for 30 seconds, after which 30 ml of fresh purified water boiled in a microwave oven for about 30 seconds was added thereto. The pentose solution was heated to boiling in a microwave oven for about 3-4 minutes, after which purified water was added thereto to a total volume of 100 ml before use in experiments. (See Table 1 above for the specific component ratio of each composition).

2-2: Preparation of Hexose Composition

A predetermined amount (3.1 g, 6.2 g or 12.4 g) of hexose (mannose, glucose or fructose) was added to 40 ml of purified water and completely dissolved by heating in a microwave oven for about 50 seconds, after which 30 ml of fresh purified water boiled in a microwave oven for about 30 seconds was added thereto. The hexose solution was heated to boiling in a microwave oven for about 2-3 minutes, after which purified water was added thereto to a total volume of 100 ml before use in experiments. (See Table 1 above for the specific component ratio of each composition).

2-3-1: Preparation 1 of Taurine+Pentose Composition

A predetermined amount (1.04 g, 2.6 g, 5.2 g, 6.5 g or 7.8 g) of pentose (xylose, arabinose or ribose) was added to 40 ml of purified water and completely dissolved by heating in a microwave oven for about 390-50 seconds. Meanwhile, (1) taurine (4.3 g) was added to 15 ml of purified water, or (2) taurine (8.6 g) was added to 30 ml of purified water, and the added taurine was dissolved by heating in a microwave oven for 40-60 seconds, after which the pentose solution prepared as described above was added thereto. The mixture was heated to boiling in a microwave oven for about 2-4 minutes, after which purified water was added thereto to a total volume of 100 ml before use in experiments. (See Table 1 above for the specific component ratio of each composition).

2-3-2: Preparation 2 of Taurine+Pentose Composition 60 ml of purified water was heated to about 100° C. in a microwave oven for 1 minute, and taurine (8.6 g) and each of arabinose (2.5 g) and xylose (3.5 g) was added thereto and completely dissolved, followed by heating in a microwave oven for 3 minutes. (See Table 1 above for the specific component ratio of each composition).

2-4: Preparation of Taurine+Hexose Composition

A predetermined amount (3.1 g or 7.75 g) of hexose (mannose, glucose or fructose) was added to 40 ml of purified water and completely dissolved by heating in a microwave oven for about 50 seconds. Meanwhile, taurine (4.3 g) was added to 15 ml of purified water and dissolved by heating in a microwave oven for 40 seconds, and then the hexose solution prepared as described above was added thereto. The mixture was heated to boiling in a microwave oven for about 2 minutes, after which purified water was added thereto to a total volume of 100 ml before use in experiments. (See Table 1 above for the specific component ratio of each composition).

2-5-1: Preparation 1 of Taurine+Polyphenol+Amino Acid Composition

Taurine (8.6 g) was added to 30 ml of purified water and completely dissolved by heating in a microwave oven for 1 minute and 20 seconds to thereby prepare an aqueous taurine solution. Meanwhile, 40 ml of purified water was heated to about 100° C. in a microwave oven for 1 minute, and catechin (3 g) and betaine (4 g) were added thereto and dissolved, after which the solution was added to the aqueous taurine solution and heated in a microwave oven for about 4 minutes. (See Table 1 above for the specific component ratio of each composition).

2-5-2: Preparation 2 of Taurine+Polyphenol+Amino Acid Composition

Taurine (8.6 g) was added to 30 ml of purified water and completely dissolved by heating in a microwave oven for 1 minute and 20 seconds to thereby prepare an aqueous taurine solution. Meanwhile, 40 ml of purified water was heated to about 100° C. in a microwave oven for 1 minute, and EGCG (1.5 g) and betaine (4 g) were added thereto and dissolved, after which the solution was added to the aqueous taurine solution and heated in a microwave oven for about 4 minutes. (See Table 1 above for the specific component ratio of each composition).

2-6: Preparation of Taurine+Polyphenol+Amino Acid+Pentose

Taurine (8.6 g) was added to 30 ml of purified water and completely dissolved by heating in a microwave oven for 1 minute and 20 seconds to thereby prepare an aqueous taurine solution. Meanwhile, 40 ml of purified water was heated to about 100° C. in a microwave oven for 1 minute, and EGCG (1.5 g), betaine (4 g) and xylose (3.5 g) were added thereto and dissolved, after which the solution was added to the aqueous taurine solution and heated in a microwave oven for about 4 minutes. (See Table 1 above for the specific component ratio of each composition).

Example 3: Analysis of Properties of Modified Taurine

Experimental Example 1: Raman Spectrum Analysis

Figure 2A:
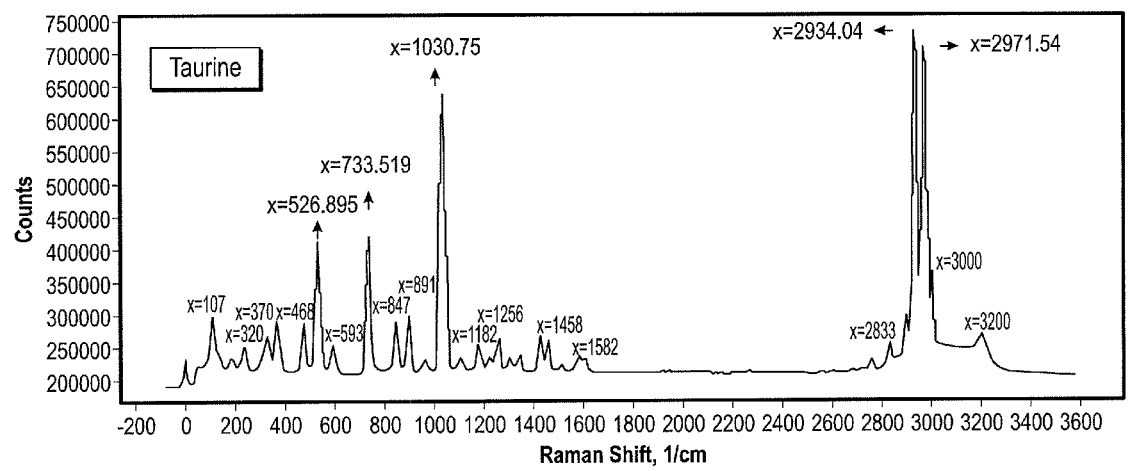
FIGS. 2(A) and 2(B) show the Raman spectra of taurine and a modified taurine according to an example of the present invention.
Figure 2B:
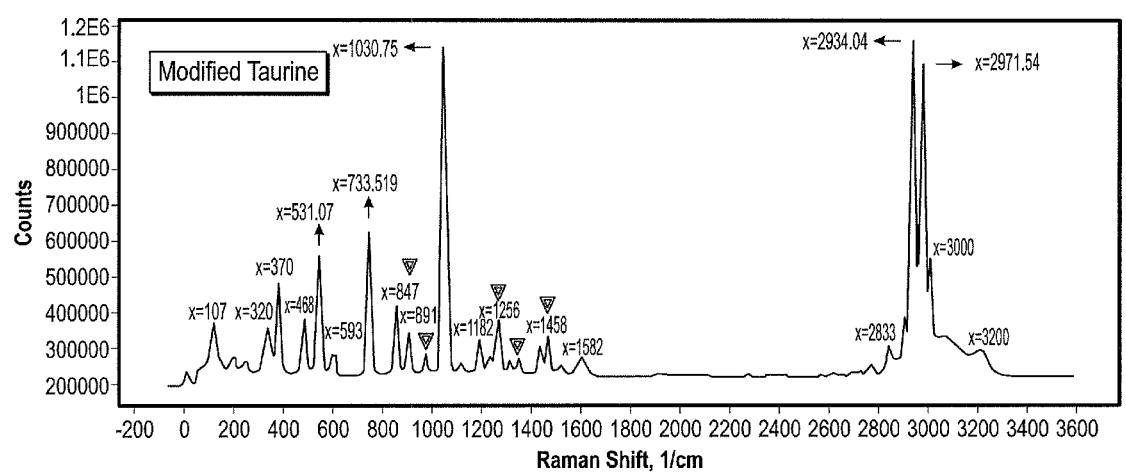

In order to examine the structural difference between taurine and the modified taurine, Raman spectrum analysis was carried out by the Korea Polymer Testing & Research Institute Ltd., and the results of the analysis are shown in FIG. 2.

The "modified taurine" crystals used in the analysis were the solid-state crystals prepared according to Example 1-2 (3).

For reference, an analysis instrument and analysis conditions are as follows.
(1) Analysis instrument: Nanofinder FLEX G (Lambda Ray)
(2) Source: 532 nm
(3) Range: 200-3600 $cm^{-1}$
(4) Exposure time, accumulation: 3 sec/20 time
(5) Spatial resolution: about 0.5 μm
(6) Peak resolution: 1 $cm^{-1}$.

As shown in FIG. 2, the "modified taurine" did somewhat differ from conventional taurine with respect to the absorption intensities of the bands at the positions indicated by red points. In a comparison with the results measured with reference to the Raman data reported in Journal of Raman Spectroscopy, Vol. 27, 507-512 (1996), it could be seen that the indicated positions were 847, 891, 1182, 1256, 1427 and 1458 $cm^{-1}$, which were all absorption bands associated with the vibration mode of $—CH_2—$ and $—C_2H_4—$ of the taurine molecule. Thus, the vibration of $—CH_2—$ and $—C_2H_4—$ in the modified taurine molecule is influenced when the modified taurine crystal is formed, and thus the modified taurine shows a difference in the Raman absorption bands. Namely, the difference in the Raman absorption bands indicates that taurine and the modified taurine differ from each other with respect to molecular physical properties.

Experimental Example 2: FT-IR (Fourier Transform Infrared Spectroscopy) Analysis In order to examine the structural difference between taurine and the modified taurine, FT-IR spectroscopy analysis was carried out by the Korea Polymer Testing & Research Institute Ltd., and the results of the analysis are shown in FIG. 3.

For reference, an analysis instrument and analysis conditions are as follows.
(1) Analysis instrument: JASCO FT-IR 4100
(2) Measurement mode: ATR mode
(3) Range: 600-4000 $cm^{-1}$
(4) Scan number: 32
(5) Peak resolution: 4 $cm^{-1}$.

Figure 3A:
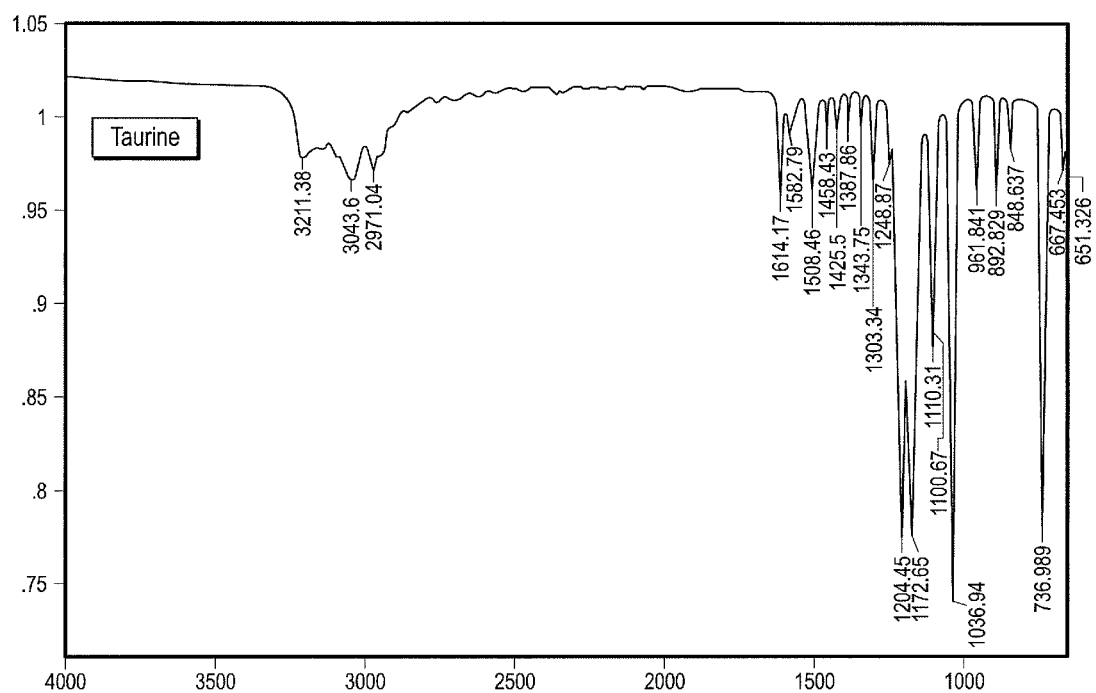
FIGS. 3(A) and 3(B) show the results of FT-IR analysis of taurine and a modified taurine according to an example of the present invention.
Figure 3B:
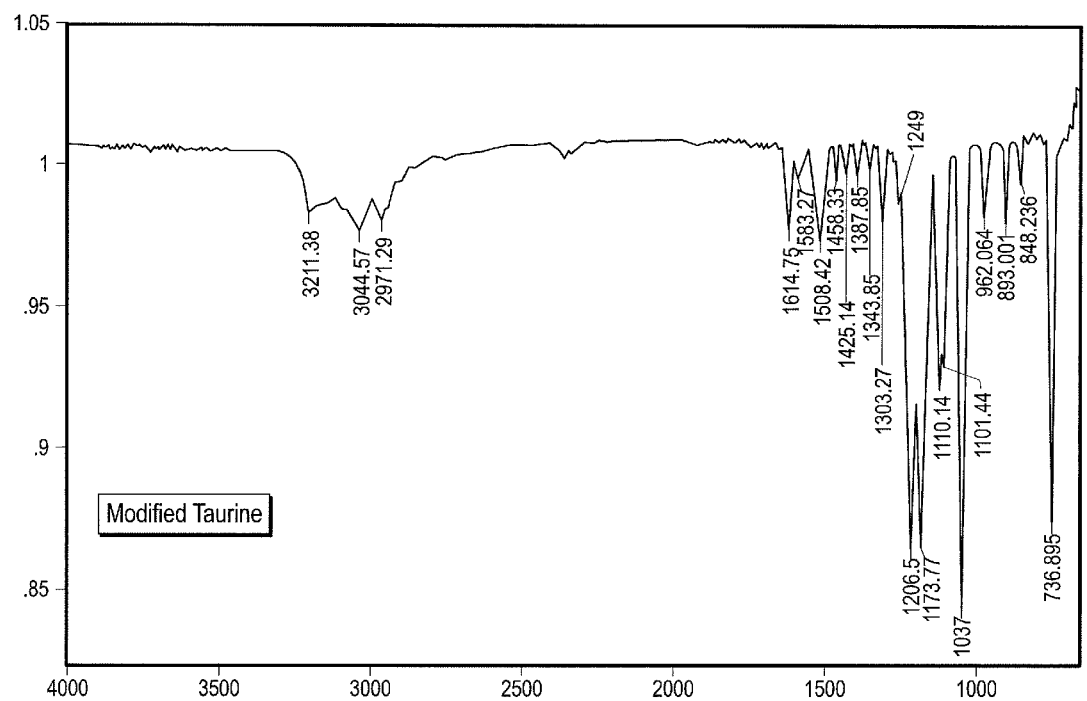

As shown in FIG. 3, the modified taurine differs from taurine with respect to the absorption wavelength at 1650-2800 $cm^{-1}$ in the FT-IR spectrum.

With reference to the data reported in Journal of Raman Spectroscopy, Vol. 27, 507-512(1996) and G. Socrates, "Infrared and Raman Characteristic Group Frequencies", John Wiley & Sons, 2001, pp. 220, this difference appears to be a characteristic that appears when the $SO_3H$ of taurine is hydrated into $SO_3^-H_3O^+$ with an external water molecule ($H_2O$). Furthermore, the vibration mode of $NH_3$ shows IR absorption at wavelengths of 1173, 1508, 1614, 3044 and 3211 $cm^{-1}$, and the vibration mode of $SO_3$ shows IR absorption at wavelengths of 1037, 1204 and 1303 $cm^{-1}$, and the IR absorption at 1527 and 3523 $cm^{-1}$ by hydrogen bonds does not appear. Thus, it can be seen that taurine and the modified taurine have the same ionized structure ($H_3N^+CH_2CH_2SO_3^-$), but there is a slight difference between the two with respect to the intensity of binding of $SO_3$ to $NH_3$ adjacent thereto in the crystals. This indicates that there is a difference in the intensity of binding between the molecules in the crystals of the ionized taurine and the ionized "modified taurine".

Experimental Example 3: Scanning Electron Microscope (SEM) Analysis

Figure 4:
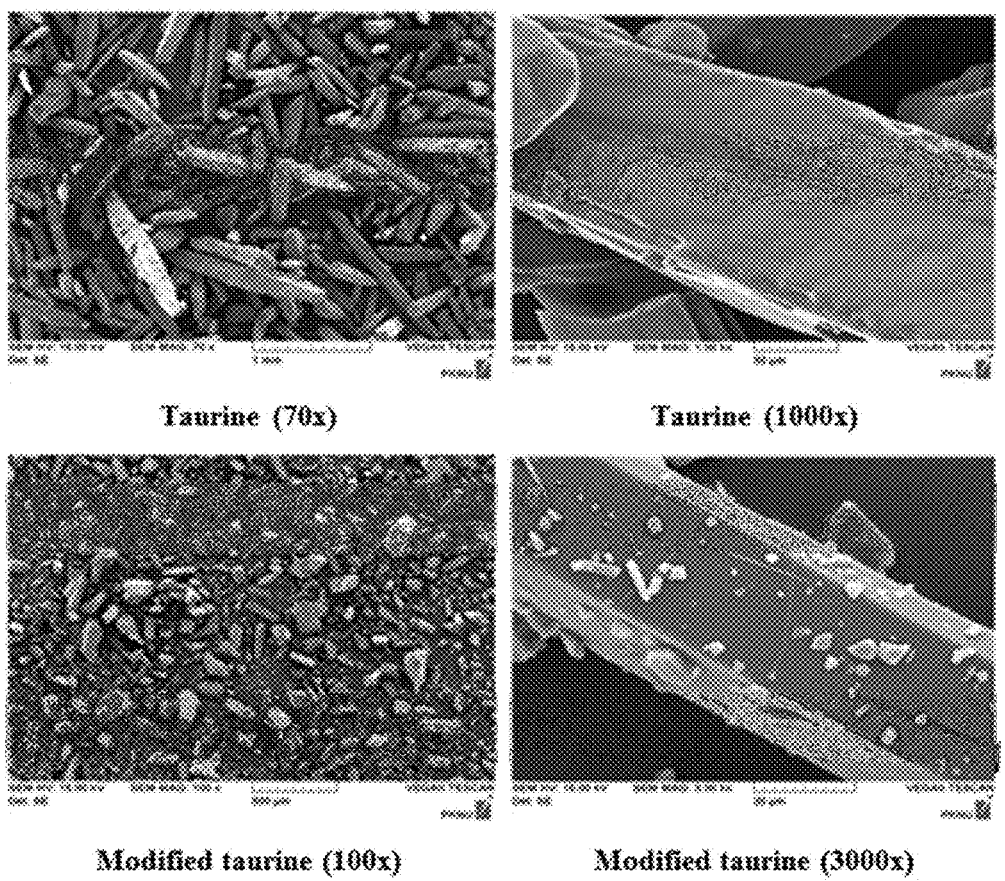
FIG. 4 shows the results of SEM analysis of taurine and a modified taurine according to an example of the present invention.

To observe the surface and morphology of each of taurine and the "modified taurine", SEM analysis was performed, and the results of the analysis are shown in FIG. 4.

For reference, an analysis instrument and analysis conditions are as follows.
(1) Analysis instrument: HITACHI (S-2700), Japan
(2) Electron gun: Tungsten filament type
(3) Resolution: 4.0 nm
(4) Accelerating voltage: 15.0 kV.

As can be seen in FIG. 4, scanning electron microscope observation indicated that taurine has a flake structure like a crystal pillar and also has a smooth surface morphology as can be seen in the enlarged view, but the "modified taurine" has a small particle size, a round particle size and a very broad particle size distribution, compared to taurine, and also contains taurine crystals. From the enlarged photograph of the modified taurine, it could be seen that the modified taurine adheres to the surface of taurine. This morphology indicates that small spherical particles were formed by water and "the polar substance having a methyl group ($—CH_3$) in its molecular structure" during the preparation process. Due to this particle shape, the modified taurine has a surface area larger than taurine having the same mass, and thus it is believed that the modified taurine will be more easily hydrated by water adsorption from air. Herein, taurine had an average particle size of 222.06 μm and a median particle size of 192.92 μm, whereas the modified taurine had an average particle size of 190.84 μm and a median particle size of 122.47 μm. Thus, it can be seen that the particle size of the modified taurine significantly differs from that of taurine.

Experimental Example 4: Thermogravimetric Analysis (TGA)

Figure 5A:
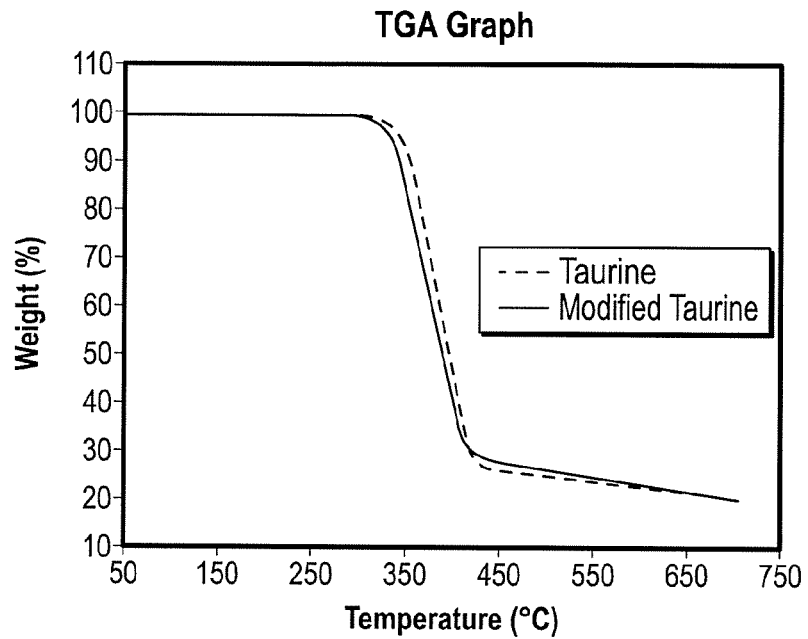
FIGS. 5(A) and 5(B) show the TGA graphs of taurine and a modified taurine according to an example of the present invention.
Figure 5B:
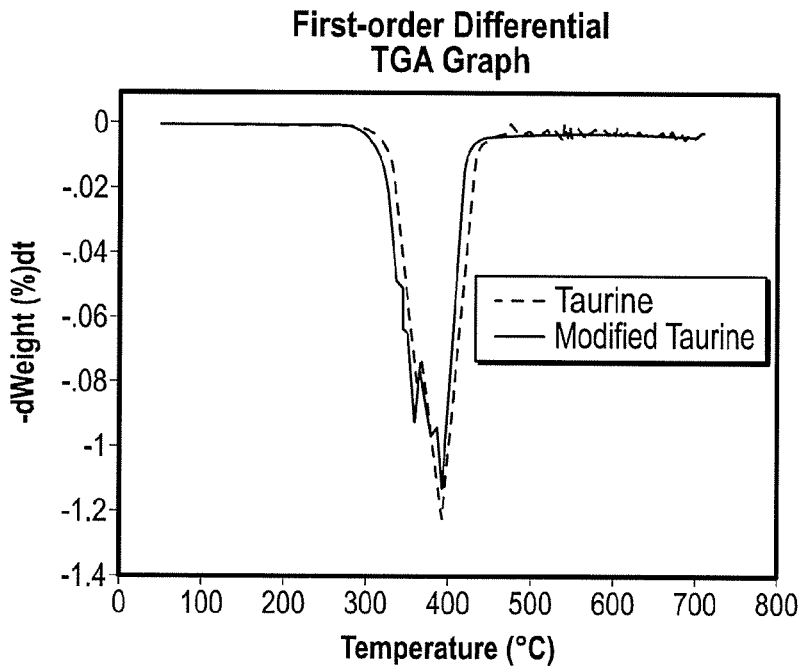

To examine the difference between taurine and the modified taurine, thermogravimetric analysis was performed, and the results of the analysis are shown in FIG. 5.

For reference, an analysis instrument and analysis conditions are as follows.
(1) Analysis instrument: TGA 7 (Perkin-Elmer)
(2) Atmosphere: $N_2$ gas
(3) Heating rate: 20° C./min
(4) Range: 50 to 600° C.

As shown in FIG. 5, TGA showed a decrease in the weight of a sample with increasing temperature. The modified taurine showed a minute decrease in the weight at 150° C. or higher, and this is believed to be because a water molecule was desorbed from hydrated $SO_3$ on the crystal surface or because a thermal decomposition reaction on the surface of very small "modified taurine" particles as shown in the SEM photograph progressed slightly fast. Small particles of the modified taurine had an increased area of exposure to heat, and thus thermally reacted faster than taurine. As shown in the first-order differentiation of TGA, the modified taurine had a first decomposition temperature of 359° C. and a final decomposition temperature of 396° C., and taurine was decomposed at 362° C. and 394° C. This is because the particle size of the modified taurine is smaller, and thus the initial thermal decomposition thereof occurs at a lower temperature, but the final decomposition temperature thereof is higher.

Experimental Example 5: Melting Point Analysis

Figure 6:
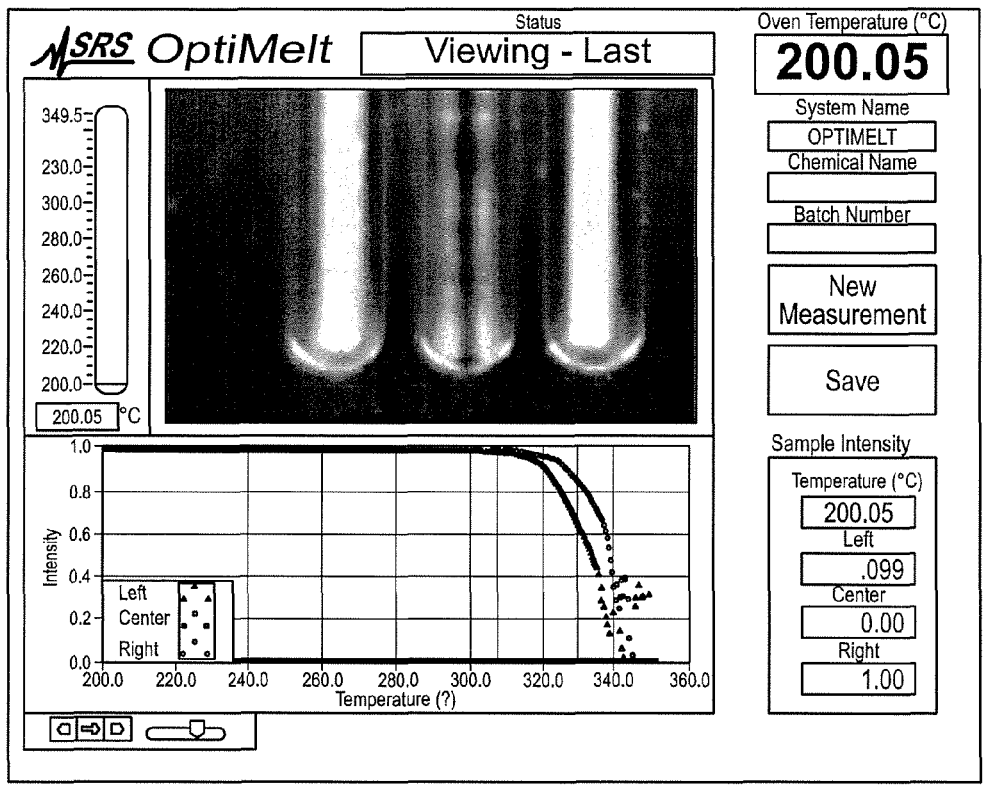
FIG. 6 shows the results of measuring the melting points of taurine and a modified taurine according to an example of the present invention.

To examine the difference between taurine and the modified taurine, malting point analysis was carried out, and the results of the analysis are shown in FIG. 6.

For reference, an analysis instrument and analysis conditions are as follows.

(1) Analysis instrument: MPA100 (SRS; Stanford Research System)
(2) Start temperature: 200° C.
(3) Heating rate: 10° C./min.

As shown in FIG. 6, the melting point (based on onset point) of the modified taurine was about 10° C. higher than that of taurine (three experimental results: 335.7° C., 336.6° C. and 337° C., respectively). This is because the intensity of binding between ionized molecules ($H_3N^+CH_2CH_2SO_3^-$) in the modified taurine crystal differs from that in taurine, as demonstrated by the absorption intensity or absorption wavelength in the Raman or FT-IR spectrum.

Experimental Example 6: Water Solubility Analysis

To examine the difference between taurine and the modified taurine, water solubility analysis (OECD Test Guideline 105) was carried by the Korea Polymer Testing & Research Institute Ltd., and the results of the analysis are shown in FIG. 7.

As shown in FIG. 7, the water solubility of taurine was 74 g/L, whereas the water solubility of the modified taurine was 77 g/L, indicating that there is a difference between water solubility between the two.

As described above, the modified taurine showed physical property values different from those of taurine.

Example 4: Examination of Theraoeutic Effect Against Metabolic Disease

Evaluation of Anticoagulant Activity

Antithrombotic (anticoagulant) activity was evaluated according to a previously reported method. Each of thromborel S, actin and thrombin, which are reagents for Sysmex CA-1500 for analysis of PT, aPTT and TT, was mounted in Sysmex CA-1500 (Siemens Healthcare, Germany) which is an automated blood coagulation test device. According to the automated procedure of the test device, clotting time (sec) (prothrombin time (PT), activated partial thromboplastin time (aPTT) and thrombin time (TT)) was measured. A sufficient amount of a sample for each of the three analyses was about 400 uL of an 80:20 mixture of plasma and a test substance.

From healthy Korean adult men, a total of 23-25 ml of blood was sampled using a vacutainer (3.2% sodium citrate) for blood coagulation testing, and then immediately, centrifuged at 4° C. and 2500 rpm for 10 minutes to isolate plasma. The isolated plasma was used in an experiment in a fresh state within 5-6 hours.

In this experiment, for the relative comparison of the measured clotting time (sec) (PT, aPTT and TT) between test groups, clotting time prolongation (%) relative to triple distilled water (purified water) that is a normal control test sample was statistically analyzed. For statistical analysis, the in vivo anticoagulant activities of test materials were comparatively analyzed using SPSS IBM version 21.0 by one-way ANOVA at $p<0.05$, and significance comparison between groups was performed by Duncan's test.

As a control material, 37.5 mg of aspirin was completely dissolved in 1 ml of ethanol, and 4 ml of purified water was added thereto to an aspirin concentration of 7.5 mg/ml. The aspirin solution was immediately used at room temperature in a light-shielded state or was cold-stored.

Figure 8A:
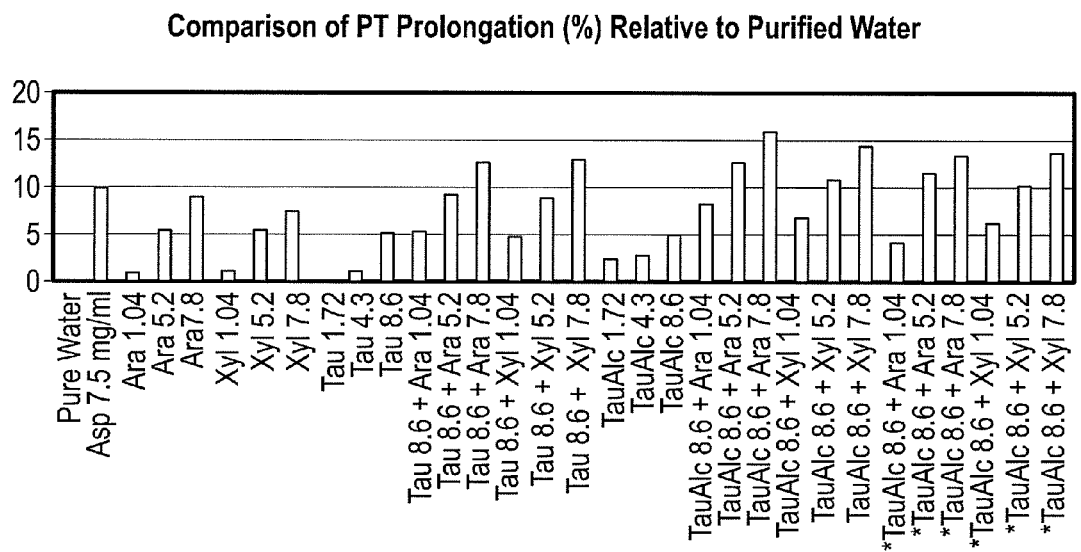
FIGS. 8(A) to 8(C) and 9(A) to 9(C) are graphs showing the results of measuring the prothrombin time, activated partial thromboplastin time and thrombin time of mice treated with the pharmaceutical composition of the present invention according to an example of the present invention.
Figure 8B:
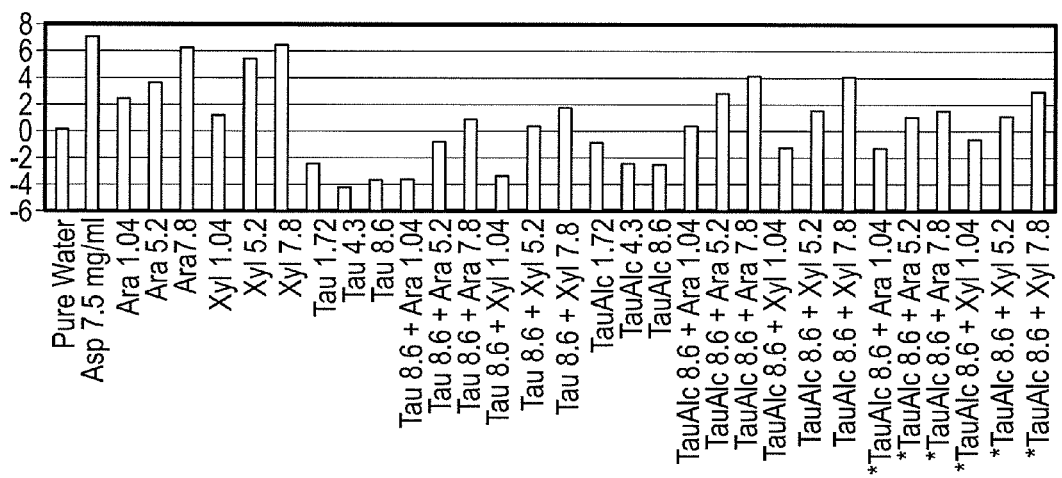
Figure 8C:
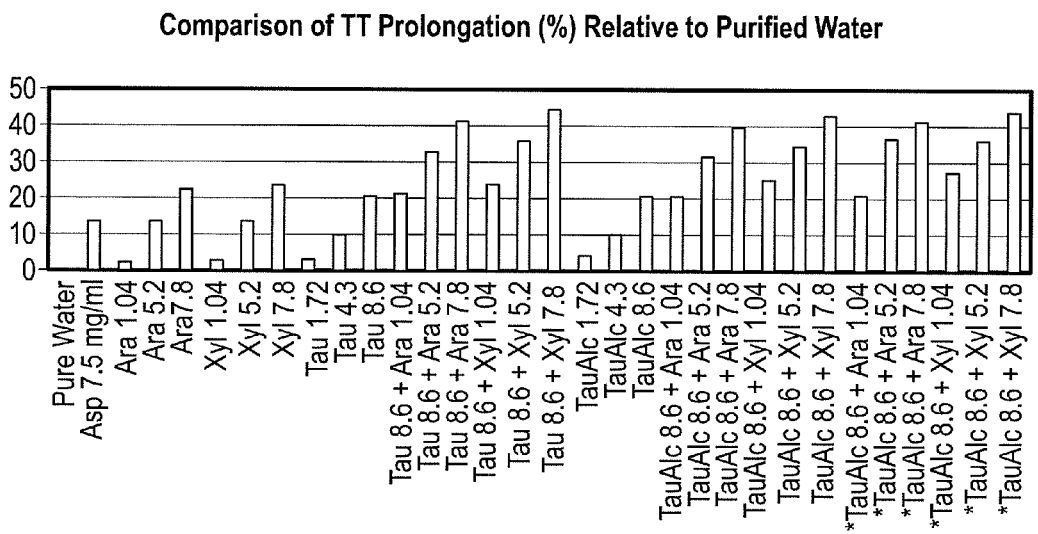
Figure 9A:
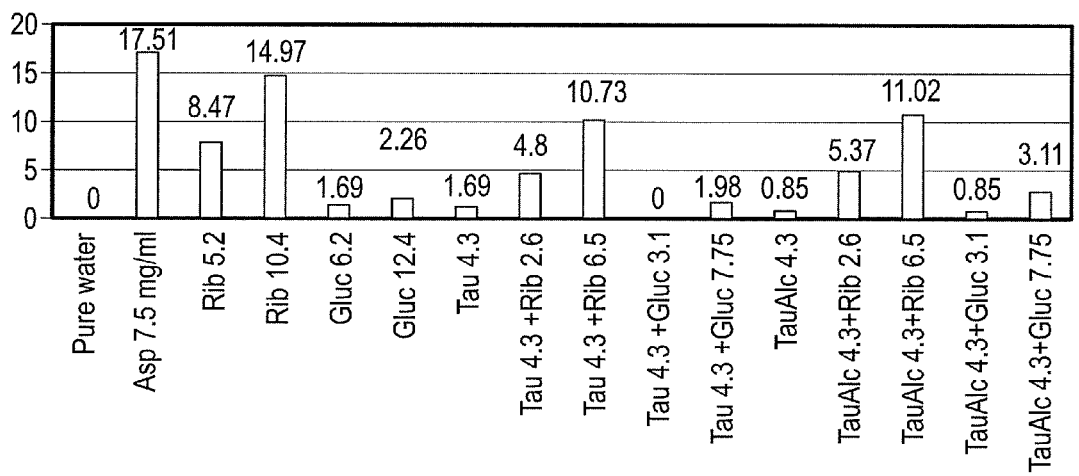
Figure 9B:
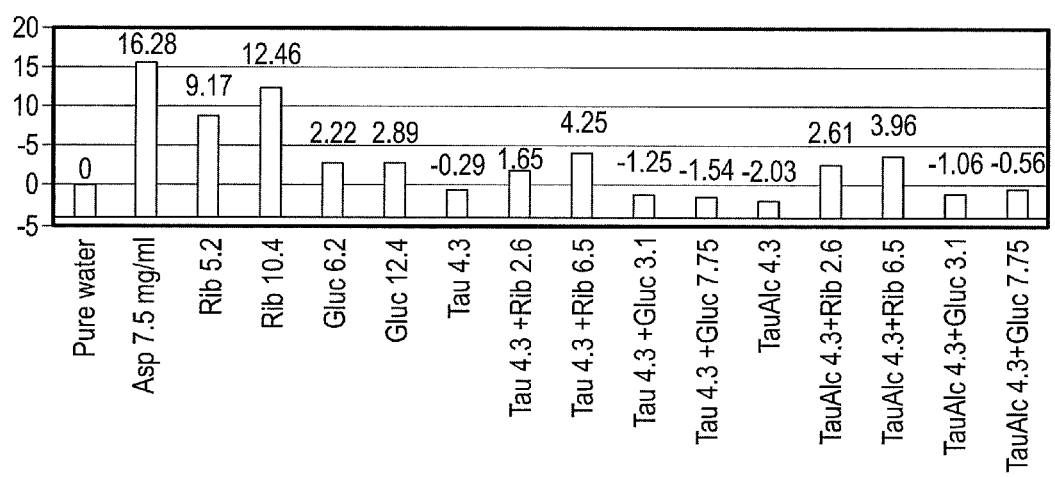
Figure 9C:
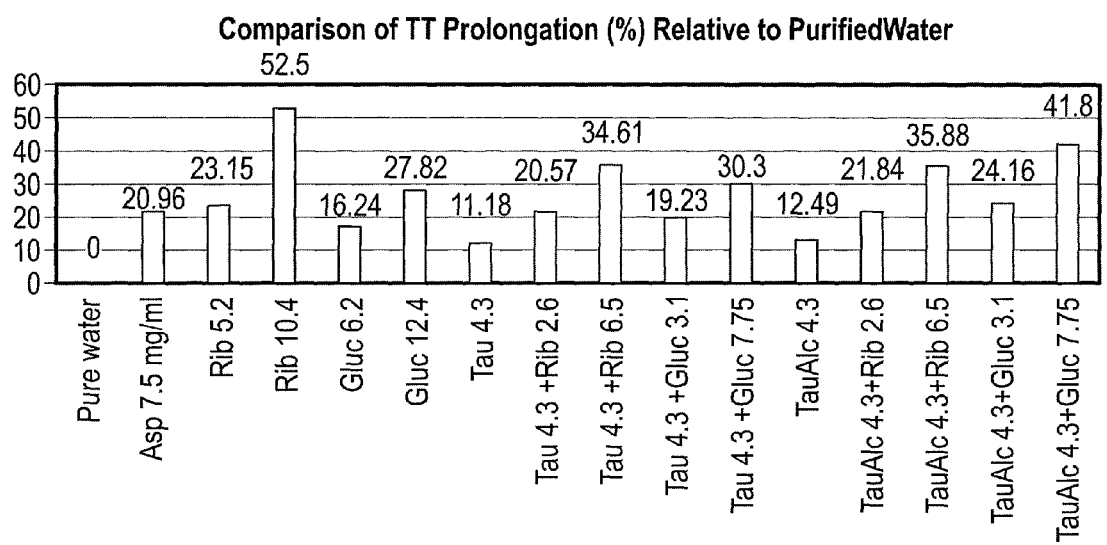
Figure 10:
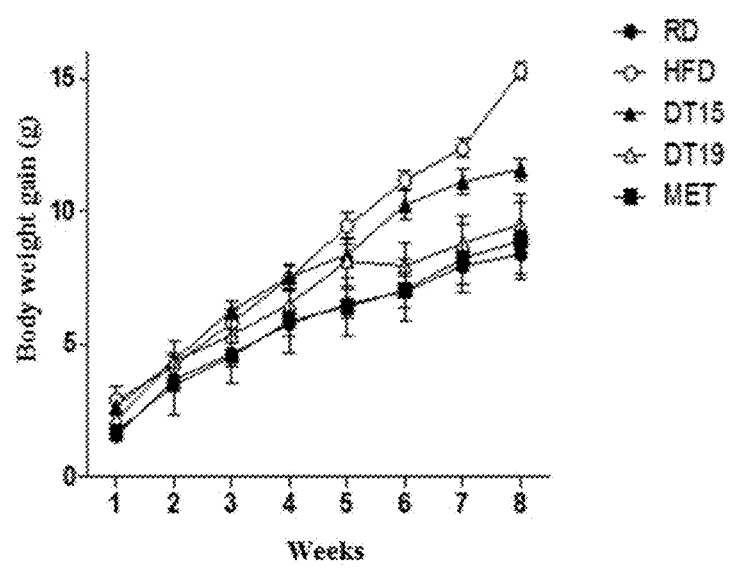
FIGS. 10(A) and (B) to 15(A) and (B) are graphs showing the body weight gain of mice treated with the pharmaceutical composition of the present invention according to an example of the present invention.
Figure 10:
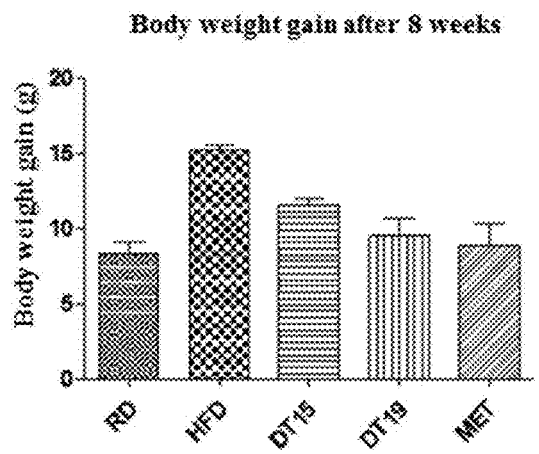
Figure 11:
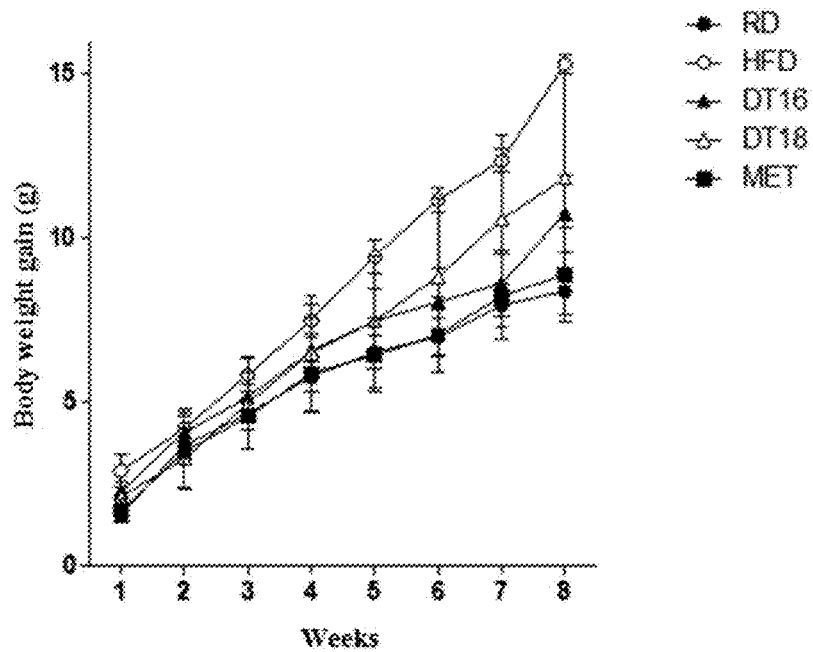
Figure 11:
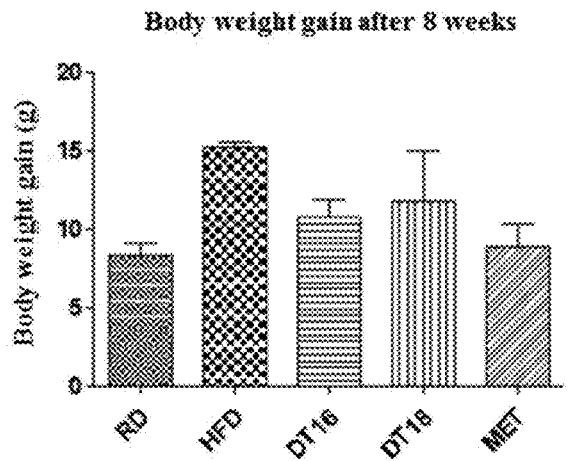
Figure 12:
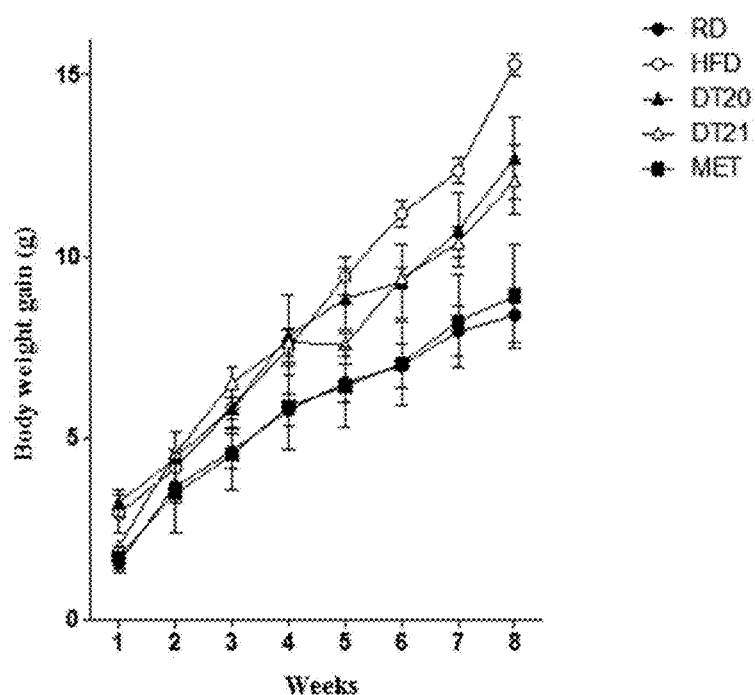
Figure 12:
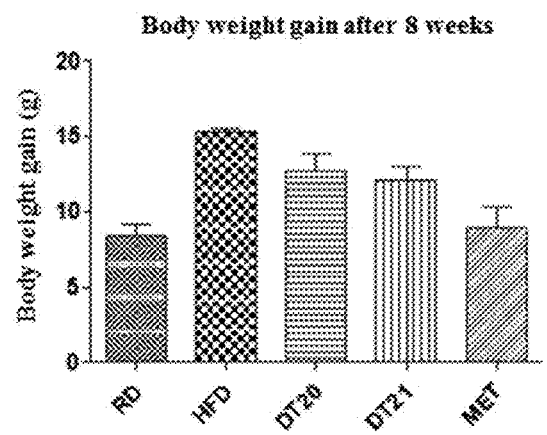
Figure 13:
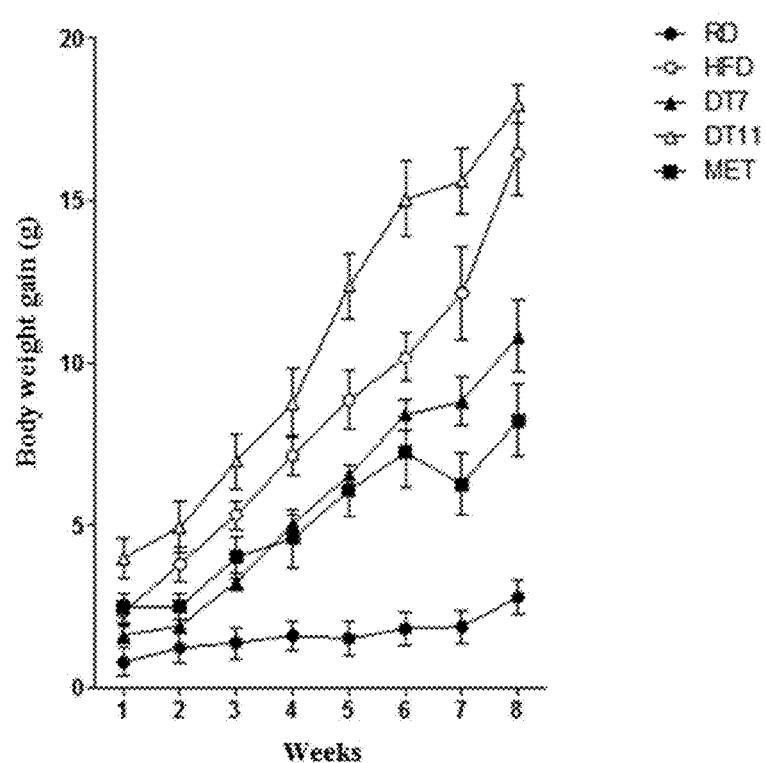
Figure 13:
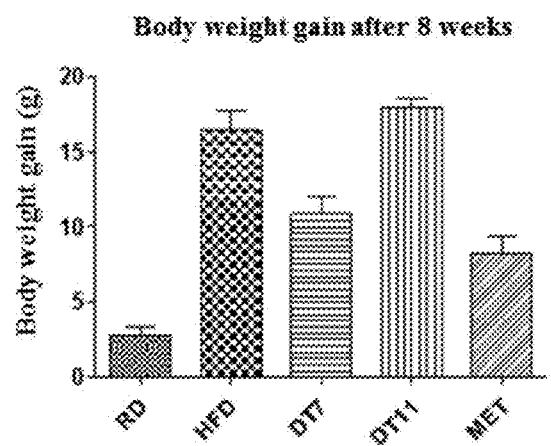
Figure 14:
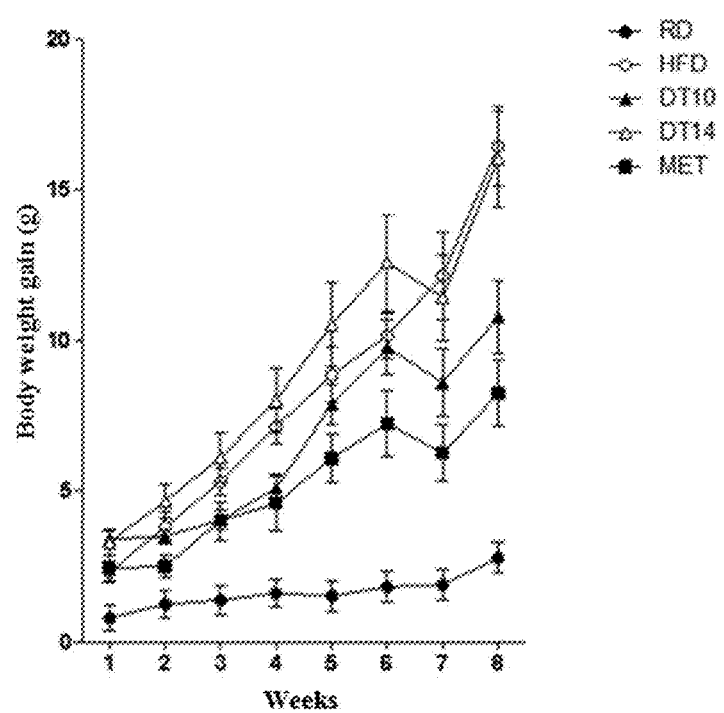
Figure 14:
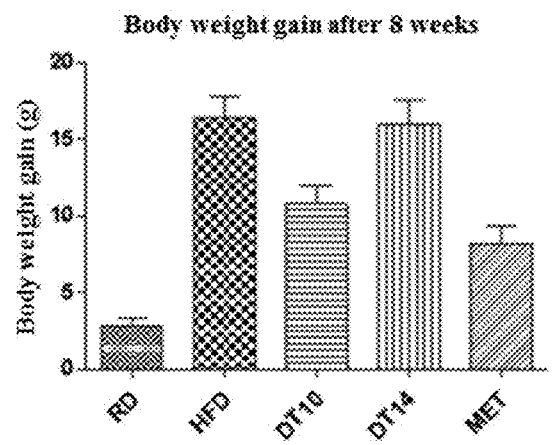
Figure 15:
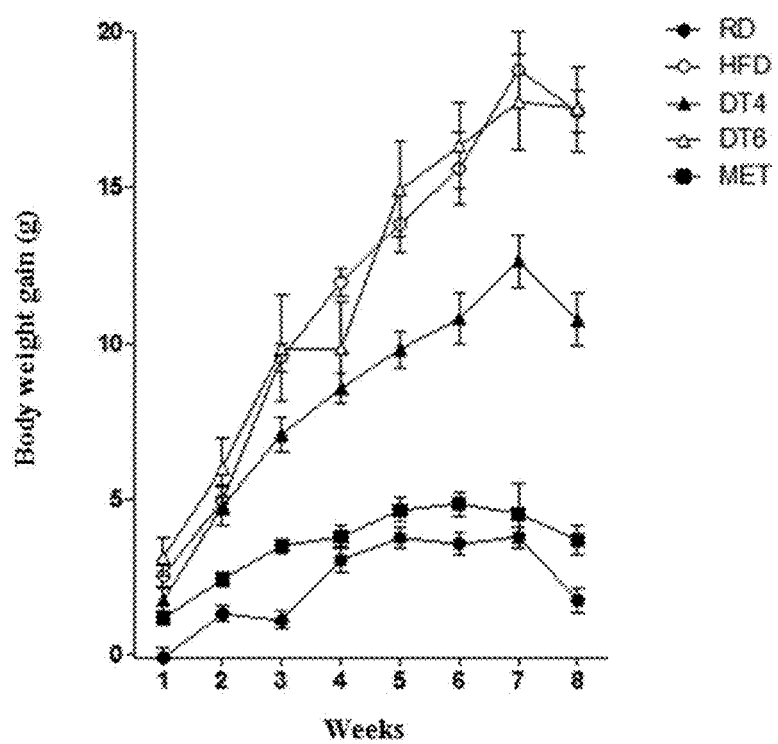
Figure 15:
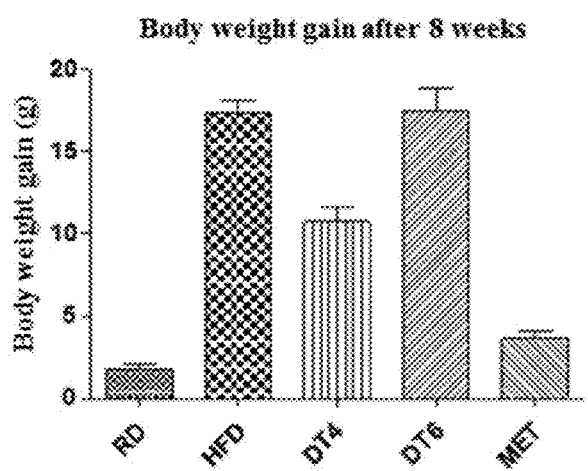
Figure 16:
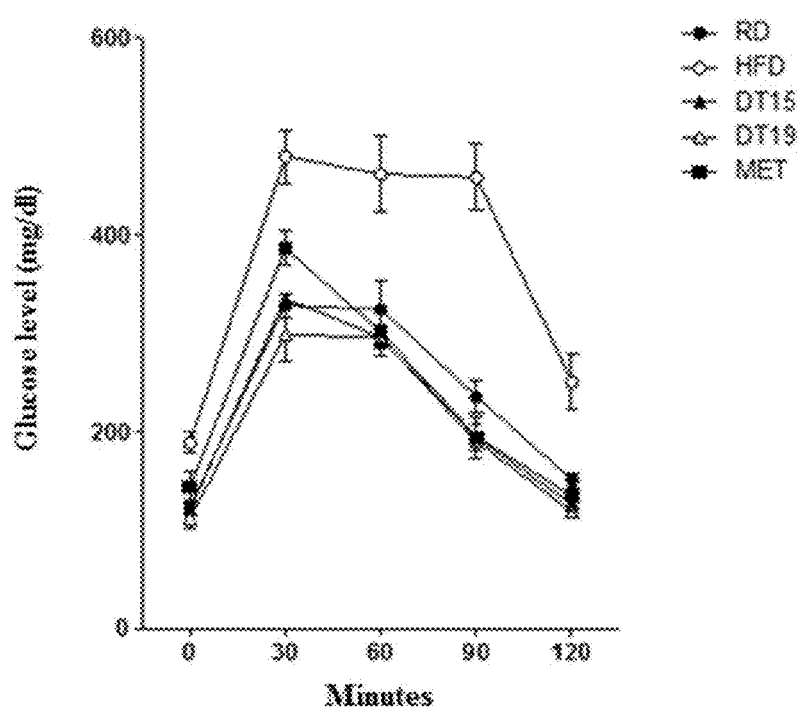
FIGS. 16 to 19 are graphs showing the results of GTT for mice treated with the pharmaceutical composition of the present invention according to an example of the present invention.
Figure 17:
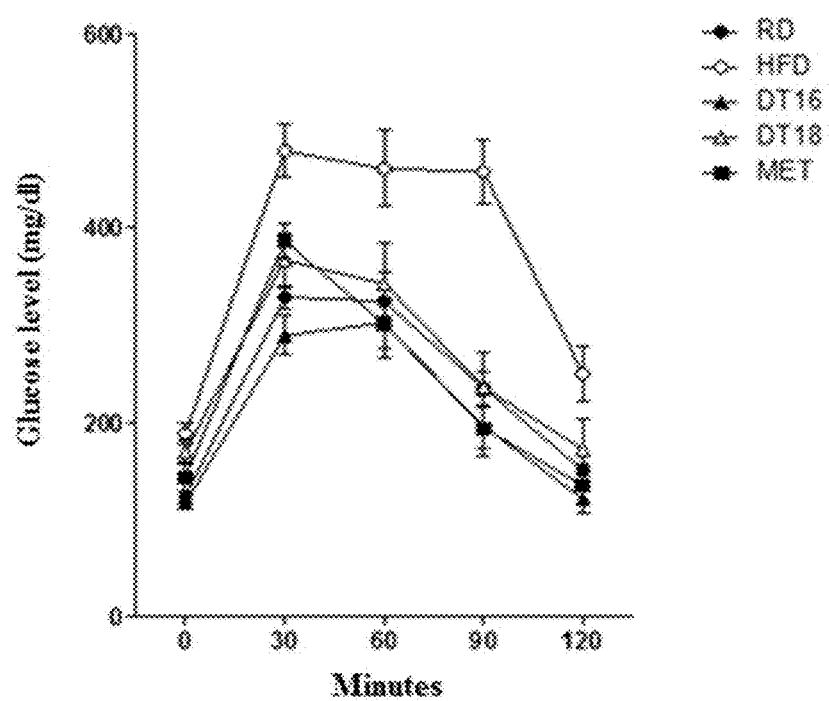
Figure 18:
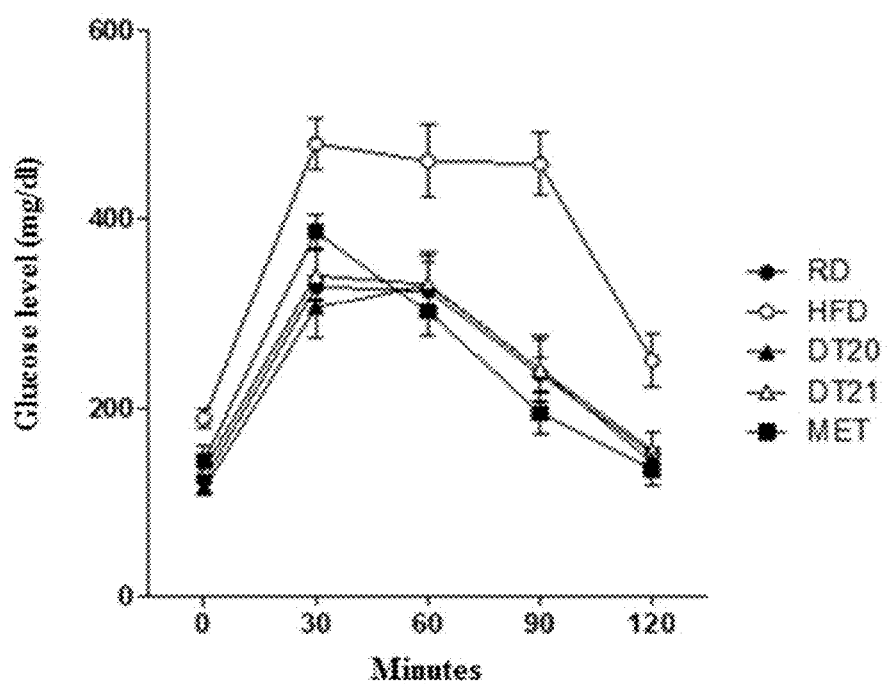
Figure 19:
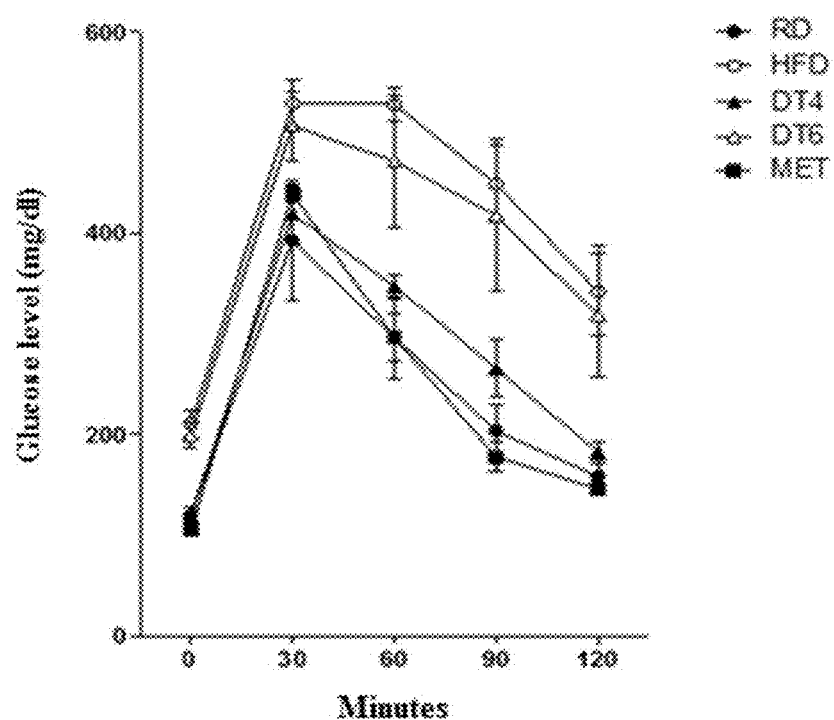

20 µl of each of the samples prepared in Examples 1 and 2 was added to 80 µl of plasma, and the plasma was measured for prothrombin time, activated partial thromboplastin time and thrombin time. The results of the measurement are shown in FIG. 8, FIG. 9 and Tables 2 to 4 below. As a control, aspirin was used, and as a vehicle control, triple distilled water (purified water) was used instead of the sample.

TABLE 2

| | | | PT | | aPTT | | TT | |
|---|---|---|---|---|---|---|---|---|
| | Test material (g/dL) | N | Mean | S.D. | Mean | S.D. | Mean | S.D. |
| Control | Purified water | 3 | 0.00 | 0.00 | 0.00 | 0.00 | 0.00 | 0.00 |
| Control | Asp 7.5 mg/Ml | 3 | 9.90 | 0.24 | 7.31 | 0.79 | 13.59 | 1.79 |
| Comparative Example 2-1 | Ara 1.04 | 3 | 0.56 | 0.98 | 2.51 | 0.92 | 2.09 | 0.53 |
| | Ara 5.2 | 3 | 5.93 | 1.47 | 3.72 | 1.76 | 13.40 | 1.01 |
| | Ara 7.8 | 3 | 9.60 | 1.29 | 6.39 | 1.90 | 22.92 | 1.22 |
| | Xyl 1.04 | 3 | 0.85 | 0.85 | 1.23 | 1.35 | 2.68 | 0.02 |
| | Xyl 5.2 | 3 | 4.52 | 1.29 | 5.70 | 0.91 | 14.59 | 1.49 |
| | Xyl 7.8 | 3 | 7.63 | 1.47 | 6.47 | 2.12 | 24.41 | 1.22 |
| Comparative Example 1-2 | Tau 1.72 | 3 | 0.00 | 0.85 | −2.41 | 0.81 | 3.58 | 0.92 |
| | Tau 4.3 | 3 | 0.56 | 0.98 | −4.35 | 1.17 | 9.83 | 1.63 |
| | Tau 8.6 | 3 | 4.80 | 1.29 | −4.01 | 0.33 | 21.13 | 0.55 |
| Example 2-3-1 | Tau 8.6 + Ara 1.04 | 3 | 4.80 | 0.49 | −4.01 | 0.41 | 22.03 | 0.69 |
| | Tau 8.6 + Ara 5.2 | 3 | 9.04 | 1.29 | −1.06 | 0.67 | 33.64 | 2.10 |
| | Tau 8.6 + Ara 7.8 | 3 | 12.71 | 1.47 | 0.83 | 1.35 | 42.57 | 1.38 |
| | Tau 8.6 + Xyl 1.04 | 3 | 4.80 | 0.98 | −3.73 | 0.85 | 24.11 | 0.22 |
| | Tau 8.6 + Xyl 5.2 | 3 | 8.76 | 0.49 | 0.47 | 1.97 | 36.32 | 1.33 |
| | Tau 8.6 + Xyl 7.8 | 3 | 12.99 | 1.29 | 1.73 | 1.95 | 45.54 | 0.77 |
| Example 1-2 | TauAlc 1.72 | 3 | 2.27 | 1.78 | −1.19 | 1.26 | 4.06 | 0.46 |
| | TauAlc 4.3 | 3 | 2.26 | 1.76 | −2.57 | 0.42 | 9.39 | 1.11 |
| | TauAlc 8.6 | 3 | 4.82 | 1.32 | −2.73 | 1.69 | 20.64 | 1.25 |
| Example 2-2-1 | TauAlc 8.6 + Ara 1.04 | 3 | 7.66 | 2.99 | 0.18 | 1.56 | 21.25 | 0.59 |
| | TauAlc 8.6 + Ara 5.2 | 3 | 12.46 | 0.43 | 2.40 | 0.54 | 32.21 | 1.68 |
| | TauAlc 8.6 + Ara 7.8 | 3 | 16.71 | 0.54 | 4.03 | 1.08 | 40.35 | 3.18 |
| | TauAlc 8.6 + Xyl 1.04 | 3 | 6.80 | 0.03 | −0.67 | 1.93 | 25.64 | 1.75 |
| | TauAlc 8.6 + Xyl 5.2 | 3 | 11.05 | 0.05 | 1.11 | 0.30 | 35.33 | 1.43 |
| | TauAlc 8.6 + Xyl 7.8 | 3 | 14.73 | 0.56 | 4.89 | 0.50 | 43.77 | 2.47 |

TABLE 2-continued

|  | Test material (g/dL) | N | PT Mean | PT S.D. | aPTT Mean | aPTT S.D. | TT Mean | TT S.D. |
|---|---|---|---|---|---|---|---|---|
| Example 2-2-2 | TauAlc 8.6 + Ara 1.04 | 3 | 4.25 | 0.87 | −1.52 | 3.58 | 21.58 | 1.26 |
|  | TauAlc 8.6 + Ara 5.2 | 3 | 11.62 | 0.52 | 1.04 | 1.70 | 37.19 | 0.52 |
|  | TauAlc 8.6 + Ara 7.8 | 3 | 13.60 | 0.07 | 1.46 | 1.06 | 41.92 | 3.15 |
|  | TauAlc 8.6 + Xyl 1.04 | 3 | 5.95 | 0.88 | −0.85 | 0.64 | 27.86 | 3.52 |
|  | TauAlc 8.6 + Xyl 5.2 | 3 | 10.20 | 0.85 | 1.46 | 1.00 | 36.27 | 1.23 |
|  | TauAlc 8.6 + Xyl 7.8 | 3 | 13.88 | 0.56 | 3.18 | 1.80 | 45.01 | 1.88 |

As shown in Table 2 above, when the modified taurine (TauAlc) was used alone or together with sugar, it showed an increase in PT prolongation compared to taurine (Tau). In the case in which the modified taurine (TauAlc) was used together with sugar, the composition containing 5.2-7.8 g of pentose (xylose (Xyl) or arabinose (Ara)) showed PT prolongation and TT prolongation, which were equal to or greater than those shown by aspirin (Asp) 7.5 mg/dL.

TABLE 3

|  | Test material (g/dL) | N | PT Mean | PT S.D. | aPTT Mean | aPTT S.D. | *TT Mean | *TT S.D. |
|---|---|---|---|---|---|---|---|---|
| Control | Purified water | 3 | 0.00 | 0.00 | 0.00 | 0.00 | 0.00 | 0.00 |
| Control | Asp 7.5 mg/Ml | 3 | 17.51 | 2.72 | 16.28 | 2.04 | 20.96 | 5.10 |
| Comparative Example 2-1 | Rib 5.2 | 3 | 8.47 | 2.24 | 9.17 | 1.42 | 23.15 | 8.20 |
|  | Rib 10.4 | 3 | 14.97 | 2.59 | 12.46 | 3.16 | 52.50 | 7.63 |
| Comparative Example 2-2 | Gluc 6.2 | 3 | 1.69 | 0.85 | 2.22 | 0.73 | 16.24 | 3.09 |
|  | Gluc 12.4 | 3 | 2.26 | 1.29 | 2.89 | 0.78 | 27.82 | 7.79 |
| Comparative Example 1-2 | Tau 4.3 | 3 | 1.69 | 0.85 | −0.29 | 1.17 | 11.18 | 5.29 |
| Comparative Example 2-3-1 | Tau 4.3 + Rib 2.6 | 3 | 4.80 | 0.49 | 1.65 | 1.03 | 20.57 | 6.88 |
|  | Tau 4.3 + Rib 6.5 | 3 | 10.73 | 0.49 | 4.25 | 0.98 | 34.61 | 6.87 |
| Comparative Example 2-4 | Tau 4.3 + Gluc 3.1 | 3 | 0.00 | 0.85 | −1.25 | 1.61 | 19.23 | 3.82 |
|  | Tau 4.3 + Gluc 7.75 | 3 | 1.98 | 1.29 | −1.54 | 1.09 | 30.30 | 4.29 |
| Example 1-2 | TauAlc 4.3 | 3 | 0.85 | 0.85 | −2.03 | 2.03 | 12.49 | 7.15 |
| Example 2-2-1 | TauAlc 4.3 + Rib 2.6 | 3 | 5.37 | 0.49 | 2.61 | 2.79 | 21.84 | 6.34 |
|  | TauAlc 4.3 + Rib 6.5 | 3 | 11.02 | 0.85 | 3.96 | 0.78 | 35.88 | 6.33 |
| Example 2-3 | TauAlc 4.3 + Gluc 3.1 | 3 | 0.85 | 0.85 | −1.06 | 1.18 | 24.16 | 4.40 |
|  | TauAlc 4.3 + Gluc 7.75 | 3 | 3.11 | 2.13 | −0.56 | 2.30 | 41.80 | 15.69 |

*Values excluding one sample showing an extreme value.

As shown in Table 3, when the modified taurine (TauAlc) was used alone or together with sugar, it showed an increase in TT prolongation compared to taurine (Tau). In the case in which the modified taurine (TauAlc) was used together with sugar, the composition containing 2.6-7.75 g of sugar (ribose (Rib) or glucose (Gluc)) showed TT prolongation equal to or greater than that shown by aspirin (Asp) 7.5 mg/dL.

TABLE 4

|  | Test material (g/dL) | N | PT Mean | PT S.D. | aPTT Mean | aPTT S.D. | TT Mean | TT S.D. |
|---|---|---|---|---|---|---|---|---|
| Control | Purified water | 3 | 0.00 | 0.00 | 0.00 | 0.00 | 0.00 | 0.00 |
| Control | Asp 7.5 mg/Ml | 3 | 26.02 | 1.41 | 29.82 | 1.78 | 23.95 | 2.18 |
| Comparative Example 2-2 | Mann 3.1 | 3 | 2.71 | 0.94 | 0.65 | 3.67 | 11.67 | 1.56 |
|  | Mann 6.2 | 3 | 5.96 | 3.29 | 1.24 | 4.22 | 22.74 | 4.59 |
|  | Mann 12.4 | 3 | 13.55 | 2.05 | 7.98 | 3.07 | 47.87 | 4.27 |
|  | Fruc 6.2 | 3 | 0.54 | 0.94 | −0.20 | 3.04 | 13.19 | 1.43 |
|  | Fruc 12.4 | 3 | 0.54 | 0.94 | 0.58 | 4.29 | 30.07 | 1.65 |
| Comparative Example 1-2 | Tau 4.3 | 3 | −3.79 | 2.35 | −5.50 | 3.82 | 9.51 | 2.10 |
| Comparative Example 2-4 | Tau 4.3 + Mann 3.1 | 3 | −1.08 | 2.35 | −3.14 | 3.83 | 17.48 | 0.78 |
|  | Tau 4.3 + Mann 7.75 | 3 | 6.23 | 1.69 | −0.02 | 3.64 | 31.60 | 2.08 |
|  | Tau 4.3 + Fruc 7.75 | 3 | 0.00 | 0.81 | −3.49 | 2.86 | 30.39 | 2.81 |
| Example 1-2 | TauAlc 4.3 | 3 | −3.79 | 2.35 | −5.45 | 2.18 | 10.12 | 0.78 |
| Example 2-3 | TauAlc 4.3 + Mann 3.1 | 3 | 0.54 | 1.88 | −2.65 | 3.33 | 18.74 | 3.05 |
|  | TauAlc 4.3 + Mann 7.75 | 2* | 5.69 | 0.00 | 1.03 | 0.37 | 34.59 | 2.63 |
|  | TauAlc 4.3 + Fruc 7.75 | 3 | −1.36 | 0.47 | −3.50 | 2.58 | 29.78 | 2.97 |

*Values excluding one sample showing an extreme value.

As shown in Table 4 above, when the modified taurine (TauAlc) was used alone or together with sugar, it showed an increase in TT prolongation compared to taurine (Tau). In the case in which the modified taurine (TauAlc) was used together with sugar, the composition containing 7.75 g of sugar (mannose (Mann) or fructose (Fruc)) showed TT prolongation equal to or greater than that shown by aspirin (Asp) 7.5 mg/dL.

Experiment on Anti-Diabetic and Anti-Obesity Effects
Experimental Method

Using 8-week-old male mice (C57BL/6) (purchased from CoreTech), anti-diabetic candidate materials were evaluated using a GTT (Glucose Tolerance Test) that is a typical method for diagnosis of diabetes.

Mice were housed at a temperature of 22±2° C. and a relative humidity of 55-60% with 12-hr light/12-hr dark cycles. Five animals were allotted to each group, and mice from the same mother were grouped into one group, because male mice tend to fight together.

As feed, high-fat diet (60% of calories from fat; Research Diet Inc., New Brunswick, N.J.) and water were fed ad libitum for 10 weeks. Herein, the water fed contained the samples prepared in Examples 1-2 (3), 2-1, 2-4-1, 2-4-2 and 2-5. As a positive control, metformin (M-072, Sigma) (250 mg/kg) was used, and as a control, the samples prepared in Comparative Examples 1-1, 2-3-2, 2-5-1, 2-5-2 and 2-6 were used.

For reference, each of the samples prepared in Examples 2-4-1, 2-4-2 and 2-5 was set to the amount to be taken by an adult man (60 kg) for 3 days, and the amount was converted into a mouse dose (12-fold/kg, see the US NIH guidance), thereby preparing animal feed. Namely, the amount to be taken by an adult man (60 kg) for 3 days is 180-day dose/kg, which corresponds to 15-day dose/kg for mice. Thus, the amount corresponds to 750-day dose/mouse (20 g), because the average weight of mice is about 20 g. Thus, one mouse was allowed to take ¹/₇₅₀ of the prepared sample each day.

In addition, each of the samples prepared in Examples 1-2 (3) and 2-1 was set to the amount to be taken by an adult man (60 kg) for 2 days, and the amount was converted into a mouse dose (12-fold/kg, see the US NIH guidance), thereby preparing animal feed. Namely, the amount to be taken by an adult man (60 kg) for 2 days is 120-day dose/kg, which corresponds to 10-day dose/kg for mice. Thus, the amount corresponds to 500-day dose/mouse (20 g), because the average weight of mice is about 20 g. Thus, one mouse was allowed to take ¹/₅₀₀ of the prepared sample each day.

The diet intake and the body weight gain were measured weekly for 8 weeks. The body weight and the diet intake were measured immediately before first drug administration, and then measured at one-week intervals.

At 8 weeks of high-fat diet feeding, a glucose tolerance test (GTT) was performed. For 8 hours for the test, mice were fasted. Then, blood was sampled from the tail vein, and initial blood glucose levels were measured with a blood glucose meter (AUTO-CHEK, Diatech Korea). Then, glucose was administered intraperitoneally to the mice at a concentration of 1 g/kg, and after 30 min, 60 min, 90 min and 120 min, blood was sampled from the mice, followed by measurement of blood glucose levels (each group consisting of five animals).

In blood biochemistry, insulin (AKRIN-011T, Shibayagi, Japan), glucose (AM202, Asan Pharmaceutical Co., Ltd., Korea), triglyceride (AM157, Asan Pharmaceutical Co., Ltd.), total cholesterol (AM202, Asan Pharmaceutical Co., Ltd.), AST and ALT (Asan Pharmaceutical Co., Ltd.) were analyzed using enzymatic assay kits.

At 10 weeks of high-fat diet feeding, the mice were sacrificed by cervical dislocation to obtain serum. For histological examination, the liver, white adipose tissue (WAT), brown adipose tissue (BAT) and kidney were fixed with formalin (50-00-0, Junsei, Japan), and the remaining organs were stored at −70° C. The blood sampled from the heart was coagulated to obtain serum which was then stored at −70° C.

For histological examination, the major organs and adipose were fixed in 4% neutral buffered formalin and embedded in paraffin blocks, and the paraffin blocks were sectioned at 5 μm and stained with hymatoxylin (MHS-16, Sigma-Aldrich, USA) and eosin (HT110116, Sigma-Aldrich). The prepared tissue samples were mounted in glycerin gel mounting media (SP15-100, Fisher Scientific, USA), covered with cover glass, and observed with a microscope (IX71, OLYMPUS, USA). The tissue was imaged with the camera equipped in the microscope.

Meanwhile, experimental analysis results were expressed as mean±S.E.M., and the significance between test groups was statistically processed using Student T-TEST, and then the significance was verified at *$P<0.05$.

Measurement Results (1) Results of Measurement of Body Weight Gain

Body weight, body weight gain and body weight T-TEST results are shown in FIGS. 10 to 15 and Tables 5 to 22 below.

TABLE 5

| | | | Weight (g) | | | | | | | | |
|---|---|---|---|---|---|---|---|---|---|---|---|
| | | | Before admis. | 1 week | 2 weeks | 3 weeks | 4 weeks | 5 weeks | 6 weeks | 7 weeks | 8 weeks |
| Control | Reference diet (RD) | Mean | 17.80 | 19.36 | 21.48 | 22.44 | 23.56 | 24.32 | 24.78 | 25.74 | 26.18 |
| | | S.D. | 0.17 | 0.35 | 0.54 | 0.56 | 0.54 | 0.57 | 0.66 | 0.78 | 0.81 |
| Control | High fat diet (HFD) | Mean | 20.68 | 23.58 | 24.87 | 26.50 | 28.16 | 30.12 | 31.85 | 33.04 | 35.96 |
| | | S.D. | 0.29 | 0.54 | 0.53 | 0.57 | 0.62 | 0.68 | 0.52 | 0.47 | 0.42 |
| Example 1-2 (3) | DT15 (TauAlc) | Mean | 17.65 | 20.30 | 22.05 | 23.93 | 25.18 | 26.03 | 27.90 | 28.75 | 29.23 |
| | | S.D. | 0.16 | 0.17 | 0.27 | 0.26 | 0.27 | 0.22 | 0.41 | 0.38 | 0.37 |
| Comp. Example 1-1 | DT19 (Tau) | Mean | 19.26 | 21.46 | 23.62 | 24.60 | 25.78 | 27.38 | 27.20 | 28.06 | 28.78 |
| | | S.D. | 0.28 | 0.35 | 0.59 | 0.66 | 0.63 | 0.77 | 0.84 | 0.97 | 1.10 |
| Control | Metformin (MET) | Mean | 19.30 | 21.00 | 22.78 | 23.84 | 25.18 | 25.72 | 26.34 | 27.52 | 28.20 |
| | | S.D. | 0.62 | 0.72 | 0.99 | 0.97 | 1.16 | 1.04 | 1.07 | 1.24 | 1.37 |

TABLE 6

| | | | Body weight gain (g) | | | | | | | |
| --- | --- | --- | --- | --- | --- | --- | --- | --- | --- | --- |
| | | | 1 week | 2 weeks | 3 weeks | 4 weeks | 5 weeks | 6 weeks | 7 weeks | 8 weeks |
| Control | Reference diet (RD) | Mean | 1.56 | 3.68 | 4.64 | 5.76 | 6.52 | 6.98 | 7.94 | 8.38 |
| | | S.D. | 0.24 | 0.45 | 0.48 | 0.44 | 0.51 | 0.59 | 0.68 | 0.73 |
| Control | High fat diet (HFD) | Mean | 2.90 | 4.19 | 5.82 | 7.48 | 9.44 | 11.17 | 12.36 | 15.28 |
| | | S.D. | 0.52 | 0.50 | 0.51 | 0.49 | 0.52 | 0.36 | 0.35 | 0.29 |
| Example 1-2 (3) | DT15 (TauAlc) | Mean | 2.65 | 4.40 | 6.28 | 7.53 | 8.38 | 10.25 | 11.10 | 11.58 |
| | | S.D. | 0.25 | 0.28 | 0.34 | 0.40 | 0.36 | 0.52 | 0.46 | 0.40 |
| Comp. Example 1-1 | DT19 (Tau) | Mean | 2.20 | 4.36 | 5.34 | 6.52 | 8.12 | 7.94 | 8.80 | 9.52 |
| | | S.D. | 0.10 | 0.73 | 0.81 | 0.74 | 0.91 | 0.91 | 1.06 | 1.12 |
| Control | Metformin (MET) | Mean | 1.70 | 3.48 | 4.54 | 5.88 | 6.42 | 7.04 | 8.22 | 8.90 |
| | | S.D. | 0.30 | 1.10 | 0.99 | 1.19 | 1.11 | 1.14 | 1.29 | 1.44 |

TABLE 7

| Group | 1 week | 2 weeks | 3 weeks | 4 weeks | 5 weeks | 6 weeks | 7 weeks | 8 weeks |
| --- | --- | --- | --- | --- | --- | --- | --- | --- |
| HFD vs DT15 | 0.7736 | 0.8052 | 0.6050 | 0.9579 | 0.2443 | 0.1925 | 0.0656 | 0.0000 |
| HFD vs DT19 | 0.3663 | 0.8499 | 0.6119 | 0.2908 | 0.1971 | 0.0016 | 0.0013 | 0.0000 |
| DT15 vs DT19 | 0.1145 | 0.9645 | 0.3648 | 0.3044 | 0.8198 | 0.0801 | 0.1116 | 0.1623 |

From Tables 5 to 7 above, it can be seen that the DT15 group administered with the modified taurine (TauAlc) and the DT19 group administered with taurine (Tau) showed a significant reduction in body weight gain compared to the group administered with high-fat diet (HFD) alone, at 8 weeks after high-fat diet (HFD) feeding.

TABLE 8

| | | | Body weight (g) | | | | | | | | |
| --- | --- | --- | --- | --- | --- | --- | --- | --- | --- | --- | --- |
| | | | Before admini. | 1 week | 2 weeks | 3 weeks | 4 weeks | 5 weeks | 6 weeks | 7 weeks | 8 weeks |
| Control | Reference diet (RD) | Mean | 17.80 | 19.36 | 21.48 | 22.44 | 23.56 | 24.32 | 24.78 | 25.74 | 26.18 |
| | | S.D. | 0.17 | 0.35 | 0.54 | 0.56 | 0.54 | 0.57 | 0.66 | 0.78 | 0.81 |
| Control | High fat diet(HFD) | Mean | 20.68 | 23.58 | 24.87 | 26.50 | 28.16 | 30.12 | 31.85 | 33.04 | 35.96 |
| | | S.D. | 0.29 | 0.54 | 0.53 | 0.57 | 0.62 | 0.68 | 0.52 | 0.47 | 0.42 |
| Example 2-1 | DT16 (TauAlc 8.6 + Ara 2.5) | Mean | 19.88 | 22.16 | 23.94 | 25.02 | 26.44 | 27.34 | 27.92 | 28.50 | 30.62 |
| | | S.D. | 0.32 | 0.32 | 0.43 | 0.53 | 0.75 | 0.71 | 0.79 | 0.74 | 0.84 |
| Comp. Example 2-3-2 | DT 18 (Tau 8.6 + Ara 2.5) | Mean | 20.20 | 22.29 | 23.47 | 25.17 | 26.70 | 27.67 | 29.03 | 30.77 | 32.03 |
| | | S.D. | 0.50 | 0.55 | 0.58 | 0.97 | 1.30 | 1.58 | 1.96 | 2.11 | 2.72 |
| Control | Metformin (MET) | Mean | 19.30 | 21.00 | 22.78 | 23.84 | 25.18 | 25.72 | 26.34 | 27.52 | 28.20 |
| | | S.D. | 0.62 | 0.72 | 0.99 | 0.97 | 1.16 | 1.04 | 1.07 | 1.24 | 1.37 |

TABLE 9

| | | | Body weight gain (g) | | | | | | | |
| --- | --- | --- | --- | --- | --- | --- | --- | --- | --- | --- |
| | | | 1 week | 2 weeks | 3 weeks | 4 weeks | 5 weeks | 6 weeks | 7 weeks | 8 weeks |
| Control | Reference diet (RD) | Mean | 1.56 | 3.68 | 4.64 | 5.76 | 6.52 | 6.98 | 7.94 | 8.38 |
| | | S.D. | 0.24 | 0.45 | 0.48 | 0.44 | 0.51 | 0.59 | 0.68 | 0.73 |
| Control | High fat diet (HFD) | Mean | 2.90 | 4.19 | 5.82 | 7.48 | 9.44 | 11.17 | 12.36 | 15.28 |
| | | S.D. | 0.52 | 0.50 | 0.51 | 0.49 | 0.52 | 0.36 | 0.35 | 0.29 |
| Example 2-1 | DT16 (TauAlc 8.6 + Ara 2.5) | Mean | 2.28 | 4.06 | 5.14 | 6.56 | 7.46 | 8.04 | 8.62 | 10.74 |
| | | S.D. | 0.29 | 0.71 | 0.75 | 1.00 | 1.00 | 1.05 | 1.02 | 1.15 |
| Comparative Example 2-3-2 | DT 18 (Tau 8.6 + Ara 2.5) | Mean | 2.09 | 3.27 | 4.97 | 6.50 | 7.47 | 8.83 | 10.57 | 11.83 |
| | | S.D. | 0.16 | 0.91 | 1.42 | 1.77 | 2.02 | 2.40 | 2.54 | 3.15 |
| Control | Metformin (MET) | Mean | 1.70 | 3.48 | 4.54 | 5.88 | 6.42 | 7.04 | 8.22 | 8.90 |
| | | S.D. | 0.30 | 1.10 | 0.99 | 1.19 | 1.11 | 1.14 | 1.29 | 1.44 |

TABLE 10

| Group | 1 week | 2 weeks | 3 weeks | 4 weeks | 5 weeks | 6 weeks | 7 weeks | 8 weeks |
|---|---|---|---|---|---|---|---|---|
| HFD vs DT16 | 0.4351 | 0.8839 | 0.4636 | 0.3673 | 0.0722 | 0.0036 | 0.0008 | 0.0002 |
| HFD vs DT18 | 0.4222 | 0.3970 | 0.4895 | 0.4556 | 0.1827 | 0.1121 | 0.2258 | 0.0582 |
| DT16 vs DT18 | 0.6482 | 0.5201 | 0.9100 | 0.9753 | 0.9974 | 0.7355 | 0.4307 | 0.7065 |

From Tables 8 to 10 above, it can be seen that the DT16 group administered with the modified taurine (TauAlc) and arabinose (Ara) showed a significant reduction in body weight gain compared to the group administered with high-fat diet (HFD) alone, at 8 weeks after high-fat diet (HFD) feeding, whereas the DT18 group administered with taurine (Tau) and arabinose (Ara) showed no significant reduction in body weight gain.

Although there was no statistically significant difference in the inhibition of body weight gain between the DT16 group and the DT18 group, it was considered in view of the difference from HFD that the body weight control effect of DT16 was greater than that of DT18.

TABLE 11

| | | | Body weight (g) | | | | | | | |
|---|---|---|---|---|---|---|---|---|---|---|
| | | | Before admini. | 1 weeks | 2 weeks | 3 weeks | 4 weeks | 5 weeks | 6 weeks | 7 weeks | 8 weeks |
| Control | Reference diet (RD) | Mean | 17.80 | 19.36 | 21.48 | 22.44 | 23.56 | 24.32 | 24.78 | 25.74 | 26.18 |
| | | S.D. | 0.17 | 0.35 | 0.54 | 0.56 | 0.54 | 0.57 | 0.66 | 0.78 | 0.81 |
| Control | High fat diet (HFD) | Mean | 20.68 | 23.58 | 24.87 | 26.50 | 28.16 | 30.12 | 31.85 | 33.04 | 35.96 |
| | | S.D. | 0.29 | 0.54 | 0.53 | 0.57 | 0.62 | 0.68 | 0.52 | 0.47 | 0.42 |
| Example 2-1 | DT20 (TauAlc 8.6 + Xyl 3.5) | Mean | 19.56 | 22.76 | 24.02 | 25.38 | 27.38 | 28.40 | 28.86 | 30.28 | 32.28 |
| | | S.D. | 0.49 | 0.67 | 0.48 | 0.76 | 0.77 | 0.88 | 1.05 | 0.94 | 0.96 |
| Comparative Example 2-3-2 | DT 21 (Tau 8.6 + Xyl 3.5) | Mean | 19.64 | 21.64 | 24.22 | 26.16 | 27.28 | 27.22 | 29.04 | 30.02 | 31.74 |
| | | S.D. | 0.15 | 0.15 | 0.10 | 0.32 | 0.27 | 0.27 | 0.16 | 0.34 | 0.81 |
| Control | Metformin (MET) | Mean | 19.30 | 21.00 | 22.78 | 23.84 | 25.18 | 25.72 | 26.34 | 27.52 | 28.20 |
| | | S.D. | 0.62 | 0.72 | 0.99 | 0.97 | 1.16 | 1.04 | 1.07 | 1.24 | 1.37 |

TABLE 12

| | | | Body weight gain (g) | | | | | | | |
|---|---|---|---|---|---|---|---|---|---|---|
| | | | 1 week | 2 weeks | 3 weeks | 4 weeks | 5 weeks | 6 weeks | 7 weeks | 8 weeks |
| Control | Reference diet (RD) | Mean | 1.56 | 3.68 | 4.64 | 5.76 | 6.52 | 6.98 | 7.94 | 8.38 |
| | | S.D. | 0.24 | 0.45 | 0.48 | 0.44 | 0.51 | 0.59 | 0.68 | 0.73 |
| Control | High fat diet (HFD) | Mean | 2.90 | 4.19 | 5.82 | 7.48 | 9.44 | 11.17 | 12.36 | 15.28 |
| | | S.D. | 0.52 | 0.50 | 0.51 | 0.49 | 0.52 | 0.36 | 0.35 | 0.29 |
| Example 2-1 | DT20 (TauAlc 8.6 + Xyl 3.5) | Mean | 3.20 | 4.46 | 5.82 | 7.82 | 8.84 | 9.30 | 10.72 | 12.72 |
| | | S.D. | 0.36 | 0.72 | 0.56 | 1.11 | 0.85 | 1.01 | 1.02 | 1.13 |
| Comparative Example 2-3-2 | DT 21 (Tau 8.6 + Xyl 3.5) | Mean | 2.00 | 4.58 | 6.52 | 7.64 | 7.58 | 9.40 | 10.38 | 12.10 |
| | | S.D. | 0.14 | 0.14 | 0.41 | 0.41 | 0.32 | 0.27 | 0.41 | 0.95 |
| Control | Metformin (MET) | Mean | 1.70 | 3.48 | 4.54 | 5.88 | 6.42 | 7.04 | 8.22 | 8.90 |
| | | S.D. | 0.30 | 1.10 | 0.99 | 1.19 | 1.11 | 1.14 | 1.29 | 1.44 |

TABLE 13

| Group | 1 week | 2 weeks | 3 weeks | 4 weeks | 5 weeks | 6 weeks | 7 weeks | 8 weeks |
|---|---|---|---|---|---|---|---|---|
| HFD vs DT20 | 0.7082 | 0.7623 | 1.0000 | 0.7485 | 0.5373 | 0.0498 | 0.0774 | 0.0118 |
| HFD vs DT21 | 0.2521 | 0.6032 | 0.3923 | 0.8377 | 0.0330 | 0.0072 | 0.0042 | 0.0012 |
| DT20 vs DT21 | 0.0154 | 0.8733 | 0.3409 | 0.8829 | 0.2028 | 0.9263 | 0.7659 | 0.6847 |

From Tables 11 to 13 above, it could be seen that the DT20 group administered with the modified taurine (TauAlc) and xylose (Ara) and the DT21 group administered with taurine (Tau) and xylose (Ara) showed a significant reduction in body weight gain compared to the group administered with high-fat diet (HFD) alone, at 8 weeks after high-fat diet (HFD) feeding.

TABLE 14

| | | | \multicolumn{9}{c}{Body weight (g)} | | | | | | | | | |
|---|---|---|---|---|---|---|---|---|---|---|---|
| | | | Before admini. | 1 week | 2 weeks | 3 weeks | 4 weeks | 5 weeks | 6 weeks | 7 weeks | 8 weeks |
| Control | Reference diet (RD) | Mean | 22.894 | 23.692 | 24.138 | 24.285 | 24.507 | 24.416 | 24.720 | 24.782 | 25.684 |
| | | S.D. | 0.599 | 0.363 | 0.442 | 0.283 | 0.183 | 0.221 | 0.321 | 0.362 | 0.170 |
| Control | High fat diet (HFD) | Mean | 22.322 | 24.642 | 26.136 | 27.642 | 29.472 | 31.176 | 32.494 | 34.478 | 38.764 |
| | | S.D. | 0.666 | 0.741 | 0.754 | 0.775 | 0.945 | 0.938 | 0.803 | 1.344 | 1.468 |
| Example 2-4-1 | DT7 (TauAlc 8.6 + Cat 3 + Bet 4) | Mean | 20.834 | 22.456 | 22.744 | 24.094 | 25.884 | 27.388 | 29.236 | 29.638 | 31.662 |
| | | S.D. | 0.660 | 0.542 | 0.519 | 0.545 | 0.701 | 0.934 | 1.114 | 1.383 | 1.727 |
| Comp. Example 2-5-1 | DT11 (Tau 8.6 + Cat 3 + Bet 4) | Mean | 20.420 | 24.418 | 25.360 | 27.388 | 29.178 | 32.794 | 35.460 | 36.012 | 38.370 |
| | | S.D. | 0.353 | 0.498 | 0.608 | 0.630 | 0.853 | 0.843 | 1.101 | 0.950 | 0.771 |
| Control | Metformin (MET) | Mean | 21.105 | 23.550 | 23.608 | 25.125 | 25.705 | 27.198 | 28.355 | 27.368 | 29.343 |
| | | S.D. | 0.568 | 0.727 | 0.794 | 0.829 | 1.034 | 1.022 | 1.101 | 1.319 | 1.516 |

TABLE 15

| | | | \multicolumn{8}{c}{Body weight gain (g)} | | | | | | | |
|---|---|---|---|---|---|---|---|---|---|---|
| | | | 1 week | 2 weeks | 3 weeks | 4 weeks | 5 weeks | 6 weeks | 7 weeks | 8 weeks |
| Control | Reference diet (RD) | Mean | 0.798 | 1.244 | 1.391 | 1.613 | 1.522 | 1.826 | 1.888 | 2.790 |
| | | S.D. | 0.444 | 0.473 | 0.475 | 0.448 | 0.507 | 0.504 | 0.499 | 0.517 |
| Control | High fat diet (HFD) | Mean | 2.320 | 3.814 | 5.320 | 7.150 | 8.854 | 10.172 | 12.156 | 16.442 |
| | | S.D. | 0.351 | 0.518 | 0.458 | 0.601 | 0.899 | 0.737 | 1.438 | 1.296 |
| Example 2-4-1 | DT7 (TauAlc 8.6 + Cat 3 + Bet 4) | Mean | 1.622 | 1.910 | 3.260 | 5.050 | 6.554 | 8.402 | 8.804 | 10.828 |
| | | S.D. | 0.251 | 0.200 | 0.259 | 0.269 | 0.334 | 0.486 | 0.733 | 1.120 |
| Comp. Example 2-5-1 | DT11 (Tau 8.6 + Cat 3 + Bet 4) | Mean | 3.998 | 4.940 | 6.968 | 8.758 | 12.374 | 15.040 | 15.592 | 17.950 |
| | | S.D. | 0.605 | 0.789 | 0.869 | 1.066 | 1.017 | 1.162 | 1.013 | 0.583 |
| Control | Metformin (MET) | Mean | 2.445 | 2.503 | 4.020 | 4.600 | 6.093 | 7.250 | 6.263 | 8.238 |
| | | S.D. | 0.442 | 0.383 | 0.637 | 0.910 | 0.795 | 1.090 | 0.944 | 1.090 |

TABLE 16

| Group | 1 week | 2 weeks | 3 weeks | 4 weeks | 5 weeks | 6 weeks | 7 weeks | 8 weeks |
|---|---|---|---|---|---|---|---|---|
| HFD vs DT7 | 0.1444 | 0.0090 | 0.0045 | 0.0128 | 0.0434 | 0.0799 | 0.0715 | 0.0112 |
| HFD vs DT11 | 0.0433 | 0.2672 | 0.1320 | 0.2253 | 0.0320 | 0.0077 | 0.0865 | 0.3197 |
| DT7 vs DT11 | 0.0067 | 0.0059 | 0.0035 | 0.0097 | 0.0006 | 0.0008 | 0.0006 | 0.0005 |

From Tables 14 to 16 above, it could be seen that the DT7 group administered with the modified taurine (TauAlc), catechin (Cat) and betaine (Bet) showed a significant reduction in body weight gain compared to the group administered with high-fat diet (HFD) alone, at 8 weeks after high-fat diet (HFD) feeding, whereas the DT1 group administered with taurine (Tau), catechin (Cat) and betaine (Bet) showed no significant reduction in body weight gain. In addition, it was considered that the body weight control effect of DT7 was significantly greater than that of DT11.

TABLE 17

Body weight (g)

| | | | Before admini. | 1 weeks | 2 weeks | 3 weeks | 4 weeks | 5 weeks | 6 weeks | 7 weeks | 8 weeks |
|---|---|---|---|---|---|---|---|---|---|---|---|
| Control | Reference | Mean | 22.894 | 23.692 | 24.138 | 24.285 | 24.507 | 24.416 | 24.720 | 24.782 | 25.684 |
| | diet (RD) | S.D. | 0.599 | 0.363 | 0.442 | 0.283 | 0.183 | 0.221 | 0.321 | 0.362 | 0.170 |
| Control | High fat | Mean | 22.322 | 24.642 | 26.136 | 27.642 | 29.472 | 31.176 | 32.494 | 34.478 | 38.764 |
| | diet (HFD) | S.D. | 0.666 | 0.741 | 0.754 | 0.775 | 0.945 | 0.938 | 0.803 | 1.344 | 1.468 |
| Example 2-4-2 | DT10 (TauAlc 8.6 + EGCG 1.5 + Bet 4) | Mean | 21.956 | 25.356 | 25.458 | 25.998 | 27.062 | 29.836 | 31.732 | 30.562 | 32.740 |
| | | S.D. | 0.483 | 0.640 | 0.524 | 0.740 | 0.666 | 0.811 | 0.946 | 0.975 | 1.135 |
| Comp. Example 2-5-2 | DT14 (Tau 8.6 + EGCG 1.5 + Bet 4) | Mean | 21.440 | 24.750 | 26.114 | 27.556 | 29.456 | 31.968 | 34.020 | 32.874 | 37.470 |
| | | S.D. | 0.638 | 0.998 | 1.142 | 1.400 | 1.654 | 2.005 | 2.181 | 2.012 | 2.186 |
| Control | Metformin | Mean | 21.105 | 23.550 | 23.608 | 25.125 | 25.705 | 27.198 | 28.355 | 27.368 | 29.343 |
| | (MET) | S.D. | 0.568 | 0.727 | 0.794 | 0.829 | 1.034 | 1.022 | 1.101 | 1.319 | 1.516 |

TABLE 18

Body weight gain (g)

| | | | 1 week | 2 weeks | 3 weeks | 4 weeks | 5 weeks | 6 weeks | 7 weeks | 8 weeks |
|---|---|---|---|---|---|---|---|---|---|---|
| Control | Reference | Mean | 0.798 | 1.244 | 1.391 | 1.613 | 1.522 | 1.826 | 1.888 | 2.790 |
| | diet (RD) | S.D. | 0.444 | 0.473 | 0.475 | 0.448 | 0.507 | 0.504 | 0.499 | 0.517 |
| Control | High fat diet (HFD) | Mean | 2.320 | 3.814 | 5.320 | 7.150 | 8.854 | 10.172 | 12.156 | 16.442 |
| | | S.D. | 0.351 | 0.518 | 0.458 | 0.601 | 0.899 | 0.737 | 1.438 | 1.296 |
| Example 2-4-2 | DT10 (TauAlc 8.6 + EGCG 1.5 + Bet 4) | Mean | 3.400 | 3.502 | 4.042 | 5.106 | 7.880 | 9.776 | 8.606 | 10.784 |
| | | S.D. | 0.274 | 0.253 | 0.330 | 0.441 | 0.683 | 0.929 | 1.126 | 1.204 |
| Comp. Example 2-5-2 | DT14 (Tau 8.6 + EGCG 1.5 + Bet 4) | Mean | 3.310 | 4.674 | 6.116 | 8.016 | 10.528 | 12.580 | 11.434 | 16.030 |
| | | S.D. | 0.407 | 0.580 | 0.850 | 1.077 | 1.412 | 1.596 | 1.414 | 1.577 |
| Control | Metformin | Mean | 2.445 | 2.503 | 4.020 | 4.600 | 6.093 | 7.250 | 6.263 | 8.238 |
| | (MET) | S.D. | 0.442 | 0.383 | 0.637 | 0.910 | 0.795 | 1.090 | 0.944 | 1.090 |

TABLE 19

| Group | 1 week | 2 weeks | 3 weeks | 4 weeks | 5 weeks | 6 weeks | 7 weeks | 8 weeks |
|---|---|---|---|---|---|---|---|---|
| HFD vs DT10 | 0.0416 | 0.6033 | 0.0536 | 0.0254 | 0.4134 | 0.7471 | 0.0879 | 0.0126 |
| HFD vs DT14 | 0.1029 | 0.3012 | 0.4338 | 0.5024 | 0.3467 | 0.2079 | 0.7296 | 0.8451 |
| DT10 vs DT14 | 0.8592 | 0.1013 | 0.0526 | 0.0369 | 0.1299 | 0.1673 | 0.1564 | 0.0295 |

From Tables 17 to 19 above, it could be seen that the DT10 group administered with the modified taurine (TauAlc), epigallocatechin gallate (EGCG) and betaine (Bet) showed a significant reduction in body weight fat compared to the group administered with high-fat diet (HFD) alone, at 8 weeks after high-fat diet (HFD) feeding, whereas DT14 administered with taurine (Tau), epigallocatechin gallate (EGCG) and betaine (Bet) showed no significant reduction in body weight gain. In addition, it was considered that the body weight control effect of DT10 was significantly greater than that of DT14.

TABLE 20

| | | | Body weight (g) | | | | | | | | |
|---|---|---|---|---|---|---|---|---|---|---|---|
| | | | Before admin. | 1 week | 2 weeks | 3 weeks | 4 weeks | 5 weeks | 6 weeks | 7 weeks | 8 weeks |
| Control | Reference diet (RD) | Mean | 25.706 | 25.614 | 27.006 | 26.814 | 28.744 | 29.442 | 29.258 | 29.476 | 27.442 |
| | | S.D. | 0.940 | 0.698 | 0.939 | 0.789 | 0.843 | 0.828 | 1.037 | 0.813 | 0.838 |
| Control | High fat diet (HFD) | Mean | 24.920 | 27.448 | 29.878 | 34.452 | 36.850 | 38.748 | 40.524 | 43.686 | 42.344 |
| | | S.D. | 0.547 | 0.453 | 0.635 | 0.725 | 0.523 | 0.548 | 0.941 | 1.164 | 0.591 |
| Example 2-5 | DT4 (TauAlc 8.6 + EGCG 1.5 + Bet 4 + Xyl 3.5) | Mean | 25.422 | 27.170 | 30.180 | 32.488 | 33.968 | 35.218 | 36.214 | 38.048 | 36.188 |
| | | S.D. | 0.237 | 0.565 | 0.800 | 0.744 | 0.642 | 0.781 | 1.038 | 1.053 | 1.044 |
| Comp. Example 2-6 | DT6 (Tau 8.6 + EGCG 1.5 + Bet 4 + Xyl 3.5) | Mean | 23.088 | 26.216 | 29.082 | 32.910 | 32.922 | 38.018 | 39.414 | 40.820 | 40.618 |
| | | S.D. | 0.690 | 1.032 | 1.372 | 2.118 | 1.931 | 2.000 | 1.890 | 2.036 | 1.784 |
| Control | Metformin (MET) | Mean | 23.938 | 25.094 | 26.344 | 27.430 | 27.708 | 28.572 | 28.772 | 28.468 | 27.608 |
| | | S.D. | 0.612 | 0.551 | 0.792 | 0.710 | 0.915 | 0.853 | 0.784 | 0.836 | 0.979 |

TABLE 21

| | | | Body weight gain (g) | | | | | | | |
|---|---|---|---|---|---|---|---|---|---|---|
| | | | 1 week | 2 weeks | 3 weeks | 4 weeks | 5 weeks | 6 weeks | 7 weeks | 8 weeks |
| Control | Reference diet (RD) | Mean | −0.092 | 1.300 | 1.108 | 3.038 | 3.736 | 3.552 | 3.770 | 1.736 |
| | | S.D. | 0.325 | 0.259 | 0.270 | 0.414 | 0.339 | 0.389 | 0.333 | 0.369 |
| Control | High-fat diet (HFD) | Mean | 2.528 | 4.958 | 9.532 | 11.930 | 13.828 | 15.604 | 18.766 | 17.424 |
| | | S.D. | 0.326 | 0.461 | 0.473 | 0.440 | 0.960 | 1.156 | 1.228 | 0.689 |
| Example 2-5 | DT4 (TauAlc 8.6 + EGCG 1.5 + Bet 4 + Xyl 3.5) | Mean | 1.748 | 4.758 | 7.066 | 8.546 | 9.796 | 10.792 | 12.626 | 10.766 |
| | | S.D. | 0.372 | 0.625 | 0.580 | 0.465 | 0.589 | 0.835 | 0.846 | 0.849 |
| Comp. Example 2-6 | DT6 (Tau 8.6 + EGCG 1.5 + Bet 4 + Xyl 3.5) | Mean | 3.128 | 5.994 | 9.822 | 9.834 | 14.930 | 16.326 | 17.732 | 17.530 |
| | | S.D. | 0.619 | 0.933 | 1.724 | 1.487 | 1.526 | 1.382 | 1.553 | 1.357 |
| Control | Metformin (MET) | Mean | 1.156 | 2.406 | 3.492 | 3.770 | 4.634 | 4.834 | 4.530 | 3.670 |
| | | S.D. | 0.180 | 0.185 | 0.223 | 0.350 | 0.398 | 0.398 | 0.936 | 0.463 |

TABLE 22

| Group | 1 week | 2 weeks | 3 weeks | 4 weeks | 5 weeks | 6 weeks | 7 weeks | 8 weeks |
|---|---|---|---|---|---|---|---|---|
| HFD vs DT4 | 0.1538 | 0.8033 | 0.0109 | 0.0007 | 0.0072 | 0.0097 | 0.0034 | 0.0003 |
| HFD vs DT6 | 0.4161 | 0.3485 | 0.8751 | 0.2135 | 0.5580 | 0.6992 | 0.6156 | 0.9462 |
| DT4 vs DT6 | 0.0924 | 0.3030 | 0.1682 | 0.4324 | 0.0138 | 0.0090 | 0.0203 | 0.0029ᵃ |

From Tables 20 to 22 above, it could be seen that the DT4 group administered with the modified taurine (TauAlc), epigallocatechin gallate (EGCG), betaine (Bet) and xylose (Xyl) showed a significant reduction in body weight gain compared to the group administered with high-fat diet (HFD) alone, at 8 weeks after high-fat diet (HFD) feeding, whereas the DT6 group administered with taurine (Tau), epigallocatechin gallate (EGCG), betaine (Bet) and xylose (Xyl) showed no significant reduction in body weight gain. In addition, it was considered that the body weight control effect of DT4 was significantly greater than that of DT6.

(2) Glucose Tolerance Test (GTT)

GTT results and T-Test results for the GTT results are shown in FIGS. 16 to 19 and Tables 23 to 30 below.

TABLE 23

|  |  | Glucose level (mg/dl) | 0 min | 30 min | 60 min | 90 min | 120 min |
| --- | --- | --- | --- | --- | --- | --- | --- |
| Control | Reference diet (RD) | Mean | 123.60 | 328.60 | 324.00 | 235.60 | 151.20 |
|  |  | S.D. | 6.44 | 12.80 | 30.00 | 16.84 | 6.57 |
| Control | High fat diet (HFD) | Mean | 188.70 | 479.70 | 461.60 | 458.40 | 250.10 |
|  |  | S.D. | 10.67 | 26.87 | 39.06 | 33.42 | 27.98 |
| Example 1-2 (3) | DT15 (TauAlc) | Mean | 121.25 | 335.25 | 295.25 | 193.75 | 126.25 |
|  |  | S.D. | 3.73 | 3.77 | 7.73 | 11.43 | 0.56 |
| Comp. Example 1-1 | DT19 (Tau) | Mean | 111.80 | 298.00 | 295.60 | 189.40 | 119.00 |
|  |  | S.D. | 11.08 | 26.76 | 11.52 | 9.75 | 6.47 |
| Control | Metformin (MET) | Mean | 144.20 | 386.40 | 301.40 | 194.40 | 135.20 |
|  |  | S.D. | 15.92 | 17.73 | 24.43 | 21.21 | 17.23 |

TABLE 24

| Group | Before administration | After 30 min | After 60 min | After 90 min | After 120 min |
| --- | --- | --- | --- | --- | --- |
| HFD vs DT15 | 0.0023 | 0.0062 | 0.0224 | 0.0004 | 0.0182 |
| HFD vs DT19 | 0.0006 | 0.0010 | 0.0119 | 0.0001 | 0.0065 |
| DT15 vs DT19 | 0.4936 | 0.2625 | 0.9822 | 0.7904 | 0.3569 |

From Tables 23 and 24 above, it could be seen that the fasting glucose levels of the DT15 group administered with the modified taurine (TauAlc) and DT19 administered with taurine (Tau) were all lower than that of the mice administered with high-fat diet (HFD), and were similar to the blood glucose levels of normal mice.

The results of the GTT indicated that the glucose control abilities of the mouse groups administered with DT15 and with DT19 all showed were significantly higher than that of the group administered with HFD alone, and the glucose control ability was similar between DT15 and DT19.

TABLE 25

|  |  | Glucose level (mg/dl) | 0 min | 30 min | 60 min | 90 min | 120 min |
| --- | --- | --- | --- | --- | --- | --- | --- |
| Control | Reference diet (RD) | Mean | 123.60 | 328.60 | 324.00 | 235.60 | 151.20 |
|  |  | S.D. | 6.44 | 12.80 | 30.00 | 16.84 | 6.57 |
| Control | High fat diet (HFD) | Mean | 188.70 | 479.70 | 461.60 | 458.40 | 250.10 |
|  |  | S.D. | 10.67 | 26.87 | 39.06 | 33.42 | 27.98 |
| Example 2-1 | DT16 (TauAlc 8.6 + Ara 2.5) | Mean | 117.00 | 289.20 | 302.20 | 196.20 | 121.40 |
|  |  | S.D. | 4.86 | 20.15 | 35.60 | 31.33 | 14.44 |
| Comp. Example 2-3-2 | DT 18 (Tau 8.6 + Ara 2.5) | Mean | 169.33 | 367.00 | 343.00 | 236.33 | 172.67 |
|  |  | S.D. | 9.21 | 22.27 | 32.94 | 28.55 | 23.62 |
| Control | Metformin (MET) | Mean | 144.20 | 386.40 | 301.40 | 194.40 | 135.20 |
|  |  | S.D. | 15.92 | 17.73 | 24.43 | 21.21 | 17.23 |

TABLE 26

| Group | Before administration | After 30 min | After 60 min | After 90 min | After 120 min |
| --- | --- | --- | --- | --- | --- |
| HFD vs DT16 | 0.0005 | 0.0005 | 0.0219 | 0.0003 | 0.0084 |
| HFD vs DT18 | 0.3740 | 0.0549 | 0.1488 | 0.0060 | 0.1848 |
| DT16 vs DT18 | 0.0029 | 0.0626 | 0.4990 | 0.4502 | 0.1322 |

From Tables 25 and 26 above, the fasting blood glucose level of the DT16 group administered with the modified taurine (TauAlc) and arabinose (Ara) was significantly lower than that of the mice administered with high-fat diet (HFD) alone, and was comparable with that of normal mice.

The results of the GTT indicated that the glucose control ability of the mice administered with DT16 was significantly higher than that of the group administered with HFD alone, and thus the blood glucose level of the mice administered with DT16 was comparable with that of normal mice. In addition, it could be seen that the glucose control effect of DT18 was better than that of DT16 and that the fasting glucose level of DT18 was significantly lower than that of DT16.

TABLE 27

| | | Glucose level (mg/dl) | 0 min | 30 min | 60 min | 90 min | 120 min |
|---|---|---|---|---|---|---|---|
| Control | Reference diet (RD) | Mean | 123.60 | 328.60 | 324.00 | 235.60 | 151.20 |
| | | S.D. | 6.44 | 12.80 | 30.00 | 16.84 | 6.57 |
| Control | High fat diet (HFD) | Mean | 188.70 | 479.70 | 461.60 | 458.40 | 250.10 |
| | | S.D. | 10.67 | 26.87 | 39.06 | 33.42 | 27.98 |
| Example 2-1 | DT20 (TauAlc 8.6 + Xyl 3.5) | Mean | 115.00 | 306.40 | 330.40 | 240.40 | 142.80 |
| | | S.D. | 7.00 | 33.04 | 35.07 | 32.68 | 15.94 |
| Comp. Example 2-3-2 | DT 21 (Tau 8.6 + Xyl 3.5) | Mean | 134.20 | 340.60 | 331.40 | 240.40 | 155.40 |
| | | S.D. | 13.04 | 27.41 | 29.45 | 35.59 | 19.60 |
| Control | Metformin (MET) | Mean | 144.20 | 386.40 | 301.40 | 194.40 | 135.20 |
| | | S.D. | 15.92 | 17.73 | 24.43 | 21.21 | 17.23 |

TABLE 28

| Group | Before administration | After 30 min | After 60 min | After 90 min | After 120 min |
|---|---|---|---|---|---|
| HFD vs DT20 | 0.0005 | 0.0019 | 0.0513 | 0.0012 | 0.0233 |
| HFD vs DT21 | 0.0089 | 0.0065 | 0.0483 | 0.0014 | 0.0440 |
| DT20 vs DT21 | 0.2306 | 0.4486 | 0.9831 | 1.0000 | 0.6314 |

From Tables 27 and 28 above, it could be seen that the fasting glucose levels of the DT20 group, administered with the modified taurine (TauAlc) and xylose (Ara), and the DT21 group administered with taurine (Tau) and xylose (Ara), were all lower than that of the mice administered with high-fat diet (HFD) alone, and were similar to the blood glucose level of normal mice.

The results of the GTT indicated that the glucose control abilities of the mouse group administered with DT20 and the mouse group administered with DT21 were significantly higher than that of the group administered with HFD alone. In addition, it could be seen that although there was no significant difference between DT20 and DT21, DT20 group showed better effects than DT21.

TABLE 29

| | | Glucose level (mg/dl) | 0 min | 30 min | 60 min | 90 min | 120 min |
|---|---|---|---|---|---|---|---|
| Control | Reference diet (RD) | Mean | 120.60 | 392.80 | 296.00 | 203.20 | 158.60 |
| | | S.D. | 2.16 | 58.61 | 40.72 | 27.48 | 17.28 |
| Control | High fat diet (HFD) | Mean | 210.80 | 528.20 | 527.40 | 448.80 | 342.20 |
| | | S.D. | 13.79 | 23.68 | 17.28 | 37.78 | 44.72 |
| Example 2-5 | DT4 (TauAlc 8.6 + EGCG 1.5 + Bet 4 + Xyl 3.5) | Mean | 121.20 | 418.75 | 347.25 | 265.25 | 182.75 |
| | | S.D. | 7.81 | 25.89 | 10.69 | 25.07 | 9.81 |
| Comp. Example 2-6 | DT6 (Tau 8.6 + EGCG 1.5 + Bet 4 + Xyl 3.5) | Mean | 199.60 | 505.80 | 471.40 | 417.40 | 318.40 |
| | | S.D. | 13.55 | 33.81 | 65.31 | 75.23 | 61.39 |
| Control | Metformin (MET) | Mean | 104.40 | 438.40 | 296.40 | 178.00 | 146.20 |
| | | S.D. | 3.72 | 8.68 | 23.15 | 14.35 | 3.02 |

TABLE 30

| Group | Before administration | After 30 min | After 60 min | After 90 min | After 120 min |
|---|---|---|---|---|---|
| HFD vs DT4 | 0.0005 | 0.0211 | 0.0001 | 0.0075 | 0.0176 |
| HFD vs DT6 | 0.5783 | 0.6021 | 0.4312 | 0.7189 | 0.7620 |
| DT4 vs DT6 | 0.0010 | 0.1003 | 0.1409 | 0.1303 | 0.0949 |

From Tables 29 and 30 above, it could be seen that the fasting glucose level of the DT4 group administered with the modified taurine (TauAlc), epigallocatechin gallate (EGCG), betaine (Bet) and xylose (Xyl) was significantly lower than that of the mice administered with high-fat diet (HFD) alone, and was similar to that the blood glucose level of normal mice.

The results of the GTT indicated that the glucose control ability of the mouse group administered with DT4 was significantly higher than that of the group administered with HFD alone, but the glucose control ability of the group administered with DT6 was lower than that of the DT4 group.

(3) Results of Blood Biochemistry

The results of measurement of triglyceride, AST and ALT levels and the T-test results for the measurement results are shown in Tables 31 to 40.

TABLE 31

| | Group | | Triglyceride level (mg/dl) | AST level (IU/L) | ALT level (IU/L) |
|---|---|---|---|---|---|
| Control | Reference diet (RD) | Mean | 76.02 | 91.34 | 10.85 |
| | | S.D. | 14.42 | 7.23 | 6.20 |
| Control | High fat diet (HFD) | Mean | 148.78 | 129.70 | 24.71 |
| | | S.D. | 32.47 | 6.48 | 3.75 |

TABLE 31-continued

| | Group | | Triglyceride level (mg/dl) | AST level (IU/L) | ALT level (IU/L) |
|---|---|---|---|---|---|
| Control | Metformin (MET) | Mean | 62.99 | 110.32 | 22.80 |
| | | S.D. | 10.70 | 16.00 | 7.16 |
| Example 1-2 (3) | DT15 (TauAlc) | Mean | 53.62 | 98.96 | 14.02 |
| | | S.D. | 7.22 | 6.11 | 3.82 |
| Comp. Example 1-1 | DT19 (Tau) | Mean | 116.20 | 118.63 | 25.47 |
| | | S.D. | 13.34 | 12.02 | 8.60 |

TABLE 32

| Group | Triglyceride | AST | ALT |
|---|---|---|---|
| HFD vs DT15 | 0.0383 | 0.0118 | 0.0890 |
| HFD vs DT19 | 0.3805 | 0.4408 | 0.9372 |
| DT15 vs DT19 | 0.0066 | 0.2211 | 0.3034 |

As can be seen in Tables 31 and 32, DT15 (modified taurine) showed triglyceride, AST and ALT levels which are similar to or lower than those of normal mice. In addition, the triglyceride level of DT15 was significantly lower than that of DT19 (taurine), and the AST and ALT levels thereof were also lower than those of DT19.

TABLE 33

| | Group | | Triglyceride level (mg/dl) | AST level (IU/L) | ALT level (IU/L) |
|---|---|---|---|---|---|
| Control | Reference diet (RD) | Mean | 76.02 | 91.34 | 10.85 |
| | | S.D. | 14.42 | 7.23 | 6.20 |
| Control | High fat diet (HFD) | Mean | 148.78 | 129.70 | 24.71 |
| | | S.D. | 32.47 | 6.48 | 3.75 |
| Control | Metformin (MET) | Mean | 62.99 | 110.32 | 22.80 |
| | | S.D. | 10.70 | 16.00 | 7.16 |
| Example 2-1 | DT16 (TauAlc 8.6 + Ara 2.5) | Mean | 54.30 | 96.48 | 10.68 |
| | | S.D. | 8.66 | 3.52 | 4.15 |
| Comparative Example 2-3-2 | DT 18 (Tau 8.6 + Ara 2.5) | Mean | 66.97 | 94.51 | 7.02 |
| | | S.D. | 18.17 | 3.02 | 7.09 |

TABLE 34

| Group | Triglyceride | AST | ALT |
|---|---|---|---|
| HFD vs DT16 | 0.0402 | 0.0042 | 0.0407 |
| HFD vs DT18 | 0.1208 | 0.0076 | 0.0492 |
| DT16 vs DT18 | 0.5202 | 0.7015 | 0.6546 |

As can be seen in Tables 33 and 34 above, DT16 (modified taurine+arabinose) and DT18 (taurine+arabinose) showed AST and ALT levels which are similar to those of normal diet (RD) and which are significantly lower than those of high-fat diet (HFD). In addition, DT16 showed a triglyceride level lower than that of reference diet (RD).

TABLE 35

| | Group | | Triglyceride level (mg/dl) | AST level (IU/L) | ALT level (IU/L) |
|---|---|---|---|---|---|
| Control | Reference diet (RD) | Mean | 76.02 | 91.34 | 10.85 |
| | | S.D. | 14.42 | 7.23 | 6.20 |

TABLE 35-continued

| | Group | | Triglyceride level (mg/dl) | AST level (IU/L) | ALT level (IU/L) |
|---|---|---|---|---|---|
| Control | High fat diet (HFD) | Mean | 148.78 | 129.70 | 24.71 |
| | | S.D. | 32.47 | 6.48 | 3.75 |
| Control | Metformin (MET) | Mean | 62.99 | 110.32 | 22.80 |
| | | S.D. | 10.70 | 16.00 | 7.16 |
| Example 2-1 | DT20 (TauAlc 8.6 + Xyl 3.5) | Mean | 60.81 | 100.44 | 8.67 |
| | | S.D. | 23.96 | 8.57 | 3.04 |
| Comp. Example 2-3-2 | DT 21 (Tau 8.6 + Xyl 3.5) | Mean | 42.35 | 85.41 | 6.76 |
| | | S.D. | 5.26 | 2.97 | 0.71 |

TABLE 36

| Group | Triglyceride | AST | ALT |
|---|---|---|---|
| HFD vs DT20 | 0.0609 | 0.0261 | 0.0105 |
| HFD vs DT21 | 0.0120 | 0.0003 | 0.0015 |
| DT20 vs DT21 | 0.4732 | 0.1363 | 0.5582 |

As can be seen in Tables 35 and 36 above, DT20 (modified taurine+xylose) and DT18 (taurine+xylose) showed AST and ALT levels which are similar to those of reference diet (RD) and which are significantly lower than those of high-fat diet (HFD). In addition, DT20 and DT21 showed triglyceride levels lower than that of reference diet (RD).

TABLE 37

| | Group | | Triglyceride level | AST level (IU/L) | ALT level (IU/L) |
|---|---|---|---|---|---|
| Control | Reference diet (RD) | Mean | 113.61 | 10.30 | 5.32 |
| | | S.D. | 22.21 | 1.41 | 0.33 |
| Control | High fat diet (HFD) | Mean | 135.37 | 21.60 | 13.31 |
| | | S.D. | 22.74 | 4.33 | 3.96 |
| Control | Metformin (MET) | Mean | 107.14 | 16.06 | 8.05 |
| | | S.D. | 10.29 | 0.99 | 0.72 |
| Example 2-4-1 | DT7 (TauAlc 8.6 + Cat 3 + Bet 4) | Mean | 100.68 | 11.41 | 7.01 |
| | | S.D. | 7.23 | 1.71 | 1.07 |

TABLE 38

| Group | Triglyceride | AST | ALT |
|---|---|---|---|
| HFD vs DT7 | 0.451 | 0.071 | 0.176 |

As can be seen in Tables 37 and 38 above, DT7 (modified taurine+catechin+betaine) showed AST and ALT levels which are similar to those of reference diet (RD) and which are smaller than those of high-fat diet (HFD). In addition, DT7 showed a triglyceride level lower than that of reference diet (RD).

TABLE 39

| | Group | | Triglyceride level | AST level (IU/L) | ALT level (IU/L) |
|---|---|---|---|---|---|
| Control | Reference diet (RD) | Mean | 81.39 | 10.09 | 0.99 |
| | | S.D. | 17.61 | 3.35 | 0.38 |
| Control | High fat diet (HFD) | Mean | 133.80 | 26.92 | 14.79 |
| | | S.D. | 8.13 | 4.44 | 5.31 |

TABLE 39-continued

| Group | | | Triglyceride level | AST level (IU/L) | ALT level (IU/L) |
|---|---|---|---|---|---|
| Control | Metformin (MET) | Mean | 46.75 | 14.10 | 3.50 |
| | | S.D. | 16.82 | 5.08 | 1.20 |
| Example 2-5 | DT4 (TauAlc 8.6 + EGCG 1.5 + Bet 4 + Xyl 3.5) | Mean | 59.85 | 13.52 | 1.03 |
| | | S.D. | 7.61 | 2.66 | 0.43 |
| Comp. Example 2-6 | DT6 (Tau 8.6 + EGCG 1.5 + Bet 4 + Xyl 3.5) | Mean | 86.72 | 14.10 | 11.22 |
| | | S.D. | 17.42 | 5.08 | 4.19 |

TABLE 40

| Group | Triglyceride | AST | ALT |
|---|---|---|---|
| HFD vs DT4 | 0.003 | 0.0465 | 0.0565 |
| HFD vs DT6 | 0.0386 | 0.0940 | 0.6119 |
| DT4 vs DT6 | 0.2458 | 0.9284 | 0.0695 |

As can be seen in Tables 39 and 40, DT4 (modified+EGCG+betaine+xylose) showed AST and ALT levels which are similar to those of reference diet (RD) and which are significantly lower than those of high-fat diet (HFD). In addition, DT4 showed a triglyceride level lower than that of reference diet (RD).

(4) Results of Histological Examination

The results of examination of the liver, white adipose tissue (WAT), brown adipose tissue (BAT) and kidney tissue of the test mice shown in FIGS. 20 to 23.

Figure 20:
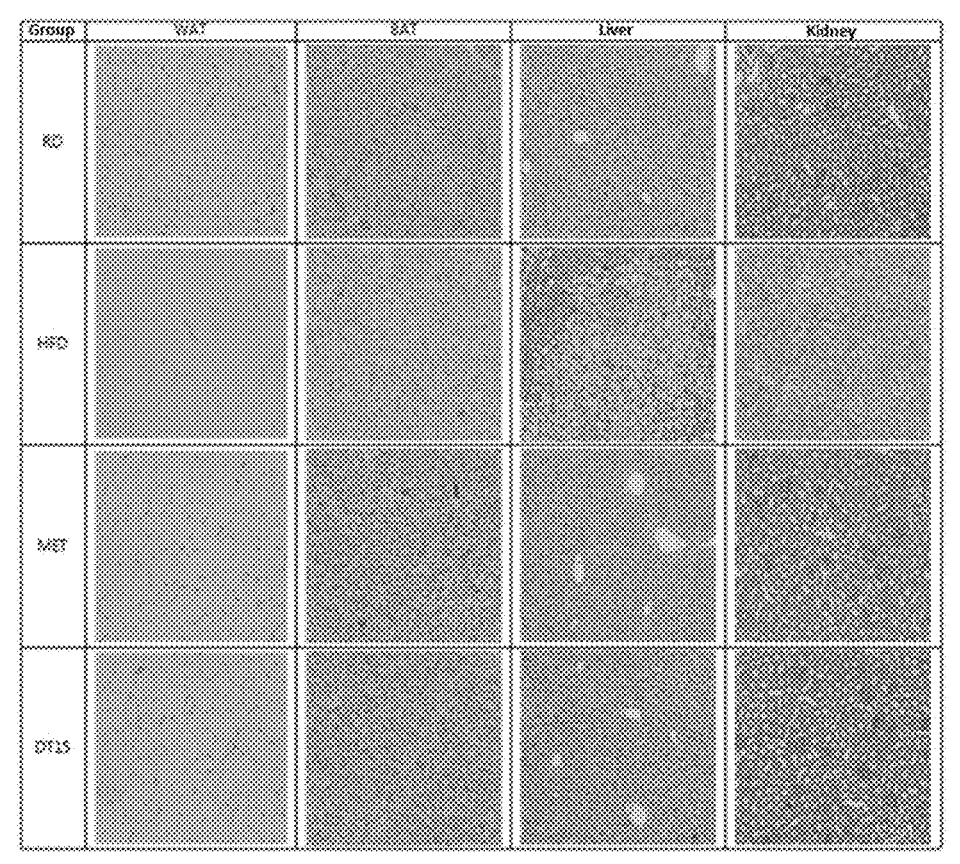

As can be seen in FIG. 20, in the case of high-fat diet (HFD), the size of adipocytes increased, the accumulation of adipose in brown adipose tissue increased, and severe fatty liver appeared. However, in the case of DT15 (modified taurine), the size of adipocytes was similar to that in the case of Metformin (MET), the accumulation of adipose in brown adipose tissue decreased, the development of fatty liver decreased, and also nephrotoxicity did not appear.

Figure 21:
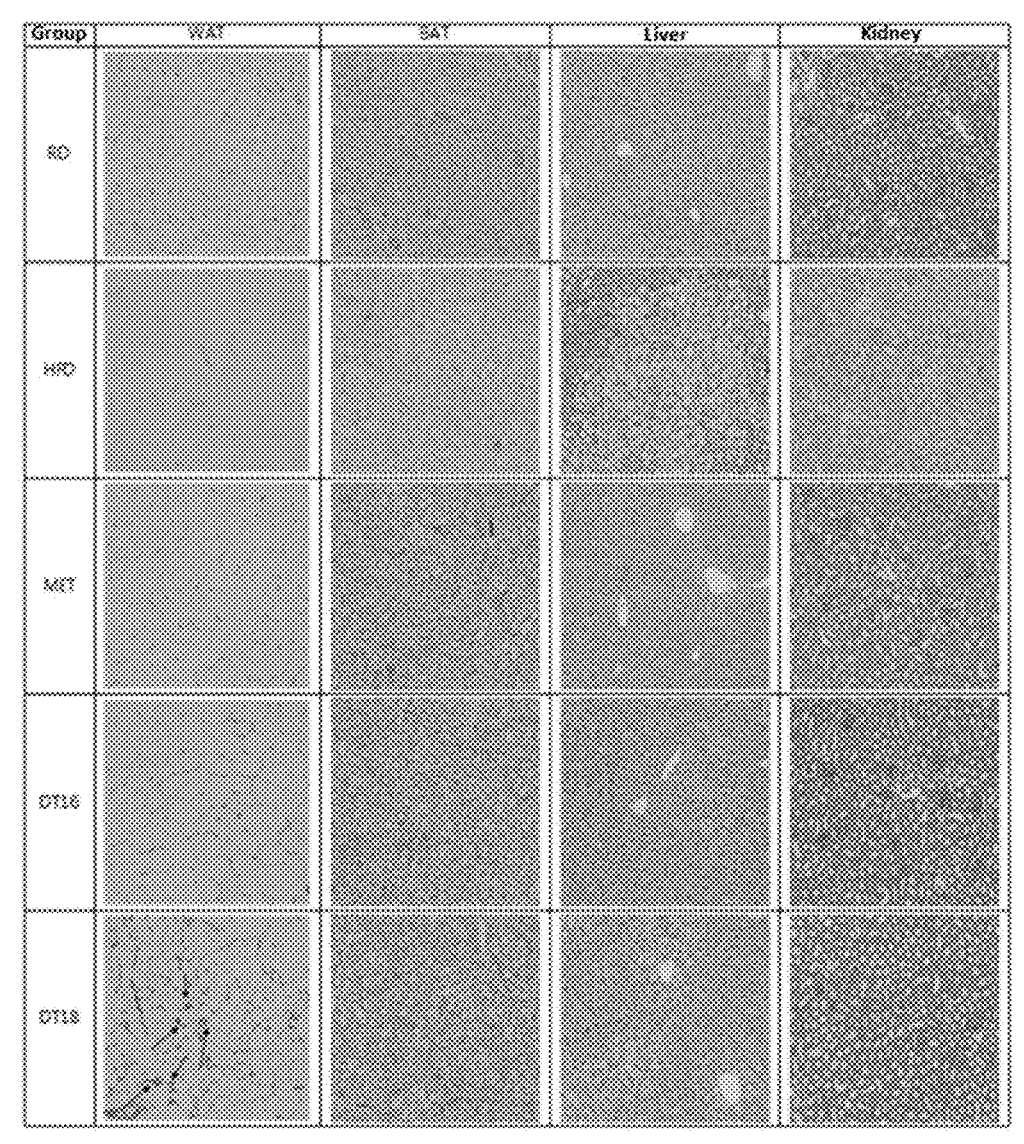

As can be seen in FIG. 21, in the case of high-fat diet (HFD), the size of adipocytes increased, the accumulation of adipose in brown adipose tissue increased, and severe fatty liver appeared. However, in the case of DT16 (modified taurine+arabinose), the accumulation of adipose in brown adipose tissue decreased, the development of fatty liver decreased, and also nephrotoxicity did not appear.

Figure 22:
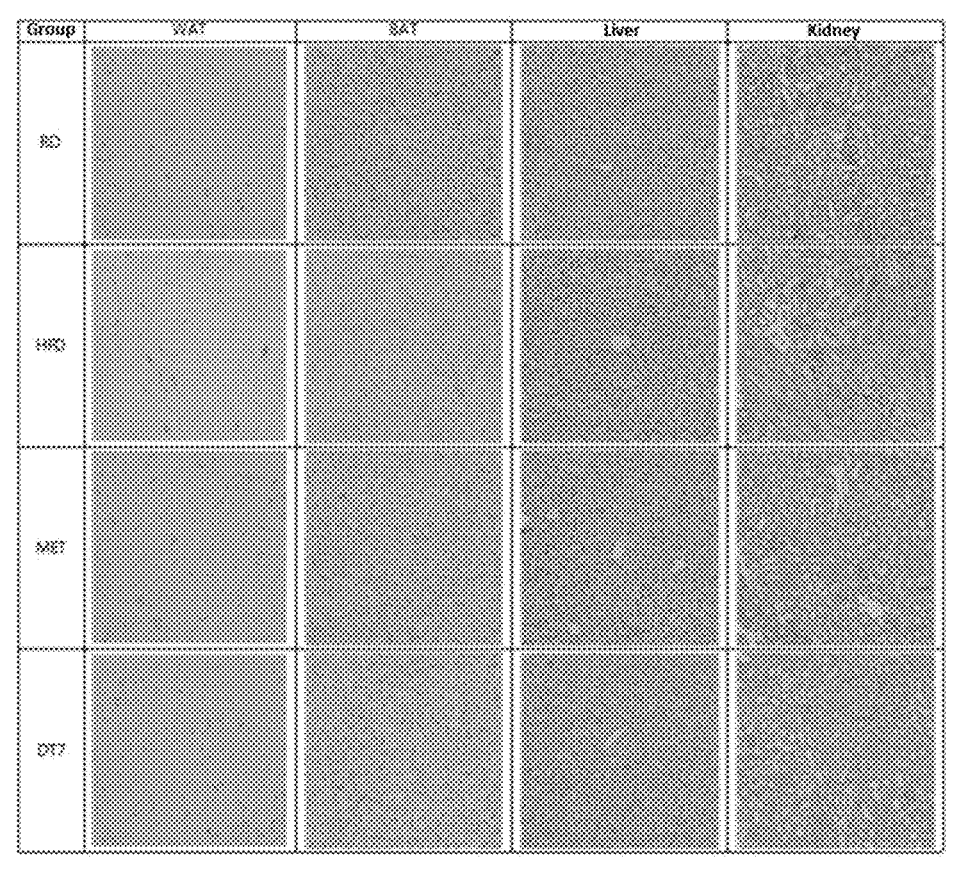

As can be seen in FIG. 22, in the case of high-fat diet (HFD), the size of adipocytes increased, the accumulation of adipose in brown adipose tissue greatly increased, the size of glomeruli increased, and severe fatty liver appeared. However, in the case of DT7 (modified taurine+catechin+betaine), the size of adipocytes decreased, the accumulation of adipose in brown adipose tissue decreased, an increase in the size of glomeruli was inhibited, the development of fatty liver decreased, and also nephrotoxicity did not appear.

Figure 23:
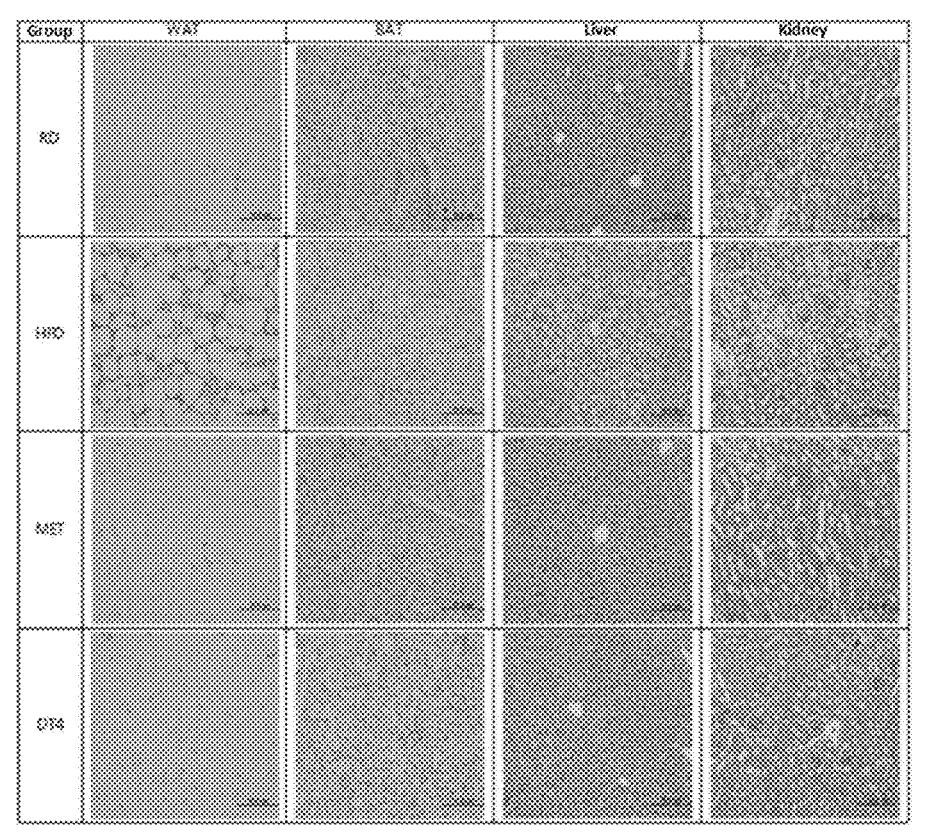

As can be seen in FIG. 23, in the case of high-fat diet (HFD), the size of adipocytes and the accumulation of macrophages between adipocytes increased, the accumulation of adipose in brown adipose tissue increased, the size of glomeruli increased, and severe fatty liver appeared. However, in the case of DT4 (modified taurine+EGCG+betaine+xylose), the size of adipocytes slightly increased, but the accumulation of macrophages did not appear, the accumulation of adipose in brown adipose tissue decreased, an increase in the size of glomeruli was inhibited, the development of fatty liver decreased, and also nephrotoxicity did not appear.

Although the present disclosure has been described in detail with reference to the specific features, it will be apparent to those skilled in the art that this description is only of a preferred embodiment thereof, and does not limit the scope of the present invention. Thus, the substantial scope of the present invention will be defined by the appended claims and equivalents thereof.

INDUSTRIAL APPLICABILITY

As described above, the modified taurine of the present invention, and a pharmaceutical composition for preventing or treating metabolic disease, which contains the modified taurine, have triglyceride-lowering effects and antithrombotic effects, and thus will greatly contribute to the prevention and treatment of metabolic syndrome.

The invention claimed is:

1. A method of treating obesity, diabetes, arteriosclerosis, or providing an anticoagulant effect, the method comprising administering to a patient in need thereof a pharmaceutical composition containing an effective amount of a modified taurine,
    wherein strength ratios of absorption bands of 891/847, 1182/1256 and 1427/1458 at 847, 891, 1182, 1256, 1427 and 1458 $cm^{-1}$ in the Raman spectrum of the modified taurine are all less than 1, the modified taurine is produced by dissolving taurine in a first polar solvent and adding a second polar solvent thereto to form a semi-solid material,
    wherein a difference in polarity between the first polar solvent and the second polar solvent is 5 or less,
    the first polar solvent is water, and the second polar solvent is any one or more selected from the group consisting of ethanol, methanol, propanol, butanol and acetone, and
    the semi-solid material is a material formed of taurine, the first polar solvent and the second polar solvent.

2. The method of claim 1, wherein the patient suffers from any one or more selected from the group consisting of myocardial infarction, ischemic stroke, hemorrhagic stroke, pulmonary thrombosis, deep vein thrombosis, peripheral vascular occlusion, portal vein thrombosis, renal vein occlusion, cerebral venous sinus thrombosis, peripheral neuropathy, peripheral vascular disease, nephropathy, and central retinal vascular occlusion.

3. The method of claim 1, wherein the pharmaceutical composition further comprises any one or more selected from the group consisting of sugar, polyphenol and amino acid.

4. The method of claim 3, wherein the pharmaceutical composition comprises sugar and the sugar is any one or more selected from the group consisting of ketotriose, aldotriose, ketotetrose, aldotetrose, ribulose, xylose, ribose, arabinose, mannose, fructose, glucose, sucrose, lactose, maltose, trehalose, inulin, and cellulose.

5. The method of claim 4, wherein a molar ratio between the modified taurine and the sugar is 0.1-3.5:0.01-3.5.

6. The method of claim 3, wherein a molar ratio between the modified taurine and the polyphenol is 0.1-3.5:0.001-3.5.

7. The method of claim 3, wherein a molar ratio between the modified taurine and the amino acid is 0.1-3.5:0.01-3.5.

8. The method of claim 3, wherein the polyphenol is catechin or epigallocatechin gallate, and the amino acid is betaine.

\* \* \* \* \*